US012508420B2

(12) United States Patent
Hanson et al.

(10) Patent No.: US 12,508,420 B2
(45) Date of Patent: Dec. 30, 2025

(54) ELECTRODE ASSEMBLY

(71) Applicant: Cirtec Medical Corporation, Brooklyn Park, MN (US)

(72) Inventors: Todd Hanson, Blaine, MN (US); Michael Miller, Minneapolis, MN (US); Daniel Oster, Centerville, MN (US); Anthony Boyle, Andover, MN (US); Gary Braegelmann, Buffalo, MN (US); Johnny Khith, Prior Lake, MN (US); Sengtavan Thammavongsa, Thammavongsa, MN (US); Jacob Zimmermann, Shorewood, MN (US); Andy Guan, Fridley, MN (US)

(73) Assignee: Cirtec Medical Corporation, Brooklyn Park, MN (US)

( * ) Notice: Subject to any disclaimer, the term of this patent is extended or adjusted under 35 U.S.C. 154(b) by 0 days.

(21) Appl. No.: 18/441,814

(22) Filed: Feb. 14, 2024

(65) Prior Publication Data

US 2024/0181245 A1 Jun. 6, 2024

Related U.S. Application Data

(62) Division of application No. 17/236,179, filed on Apr. 21, 2021, now Pat. No. 11,904,160.

(60) Provisional application No. 63/013,318, filed on Apr. 21, 2020.

(51) Int. Cl.
*A61N 1/05* (2006.01)

(52) U.S. Cl.
CPC .................................... *A61N 1/05* (2013.01)

(58) Field of Classification Search
CPC ....... A61N 1/05; A61N 1/0551; A61N 1/0553
See application file for complete search history.

(56) References Cited

U.S. PATENT DOCUMENTS 8,781,600 B2 7/2014 Janik
9,700,221 B2 7/2017 Rajaraman

*Primary Examiner* — Mark W. Bockelman
(74) *Attorney, Agent, or Firm* — Haynes and Boone, LLP

(57) ABSTRACT

An electrode assembly includes a substrate, a plurality of electrodes, and a wiring assembly. The substrate includes an elongate body extending from a first end to a second end in a first direction and a plurality of electrode connection structures connected with the elongate body. Each electrode connection structure defines a first coupling end, a second coupling end, and a first opening positioned between the first coupling end and the second coupling end. The electrodes are positioned within the plurality of electrode connection structures. A portion of each electrode extends through the first opening of the respective electrode connection structure. The wiring assembly extends along the substrate and forms an electrical connection with each of the plurality of the electrodes.

20 Claims, 37 Drawing Sheets

ELECTRODE ASSEMBLY

PRIORITY DATA

The present application is a divisional of U.S. patent application Ser. No. 17/236,179, filed Apr. 21, 2021, entitled "Electrode Assembly", which claims benefit of U.S. Provisional Patent Application No. 63/013,318, filed Apr. 21, 2020, entitled "Electrode Assembly", the disclosures of each which have been hereby incorporated by reference in their respective entireties.

BACKGROUND

Electrode assemblies are used in various different medical applications. Current electrode assemblies are connected with a stimulator to deliver electrical pulses to an area of the body for treatment. Conventional electrode assemblies and the fabrication thereof may require numerous fabrication steps (e.g., requiring multiple molds). In addition, during assembly and manufacturing, components of the electrode assemblies can be subject to misalignment and damage. Furthermore, current designs for electrode assemblies can produce a large amount of scrap material. These situations lead to a higher expense in producing suitable electrode assemblies in medical applications.

DESCRIPTION

Figure 1:
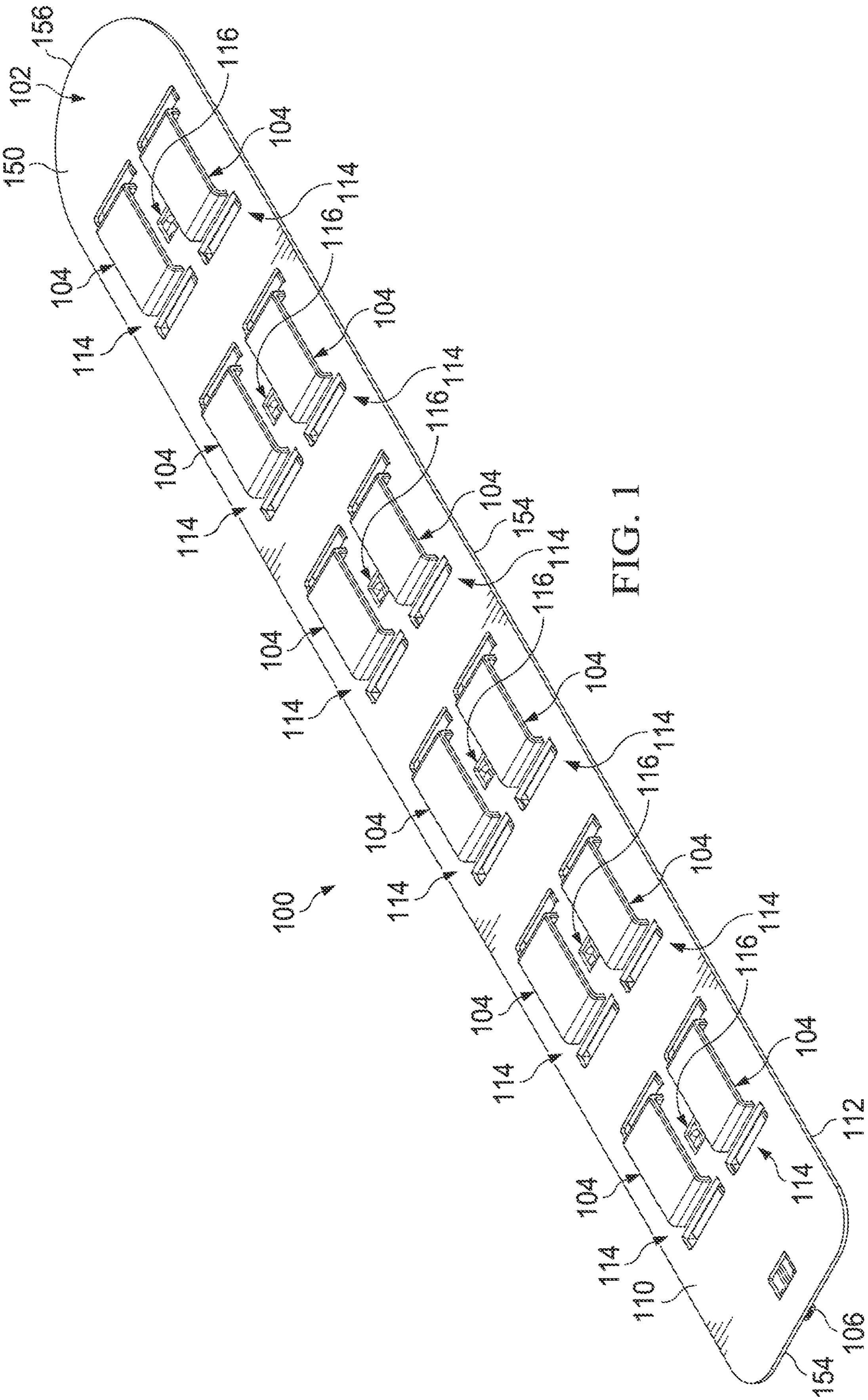
FIG. 1 is a top perspective view of an example electrode assembly according to embodiments of the present disclosure.

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

In addition, the present disclosure may repeat reference numerals and/or letters in the various examples. This repetition is for the purpose of simplicity and clarity and does not in itself dictate a relationship between the various embodiments and/or configurations discussed. Moreover, the formation of a feature on, connected to, and/or coupled to another feature in the present disclosure that follows may include embodiments in which the features are formed in direct contact, and may also include embodiments in which additional features may be formed interposing the features, such that the features may not be in direct contact. In addition, spatially relative terms, for example, "lower," "upper," "horizontal," "vertical," "above," "over," "below," "beneath," "up," "down," "top," "bottom," etc., as well as derivatives thereof (e.g., "horizontally," "downwardly," "upwardly," etc.) are used for ease of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/−10% of the number described or other values as understood by person skilled in the art. For example, the term "about 5 microns" encompasses the dimension range from 4.5 microns to 5.5 microns.

Figure 2:
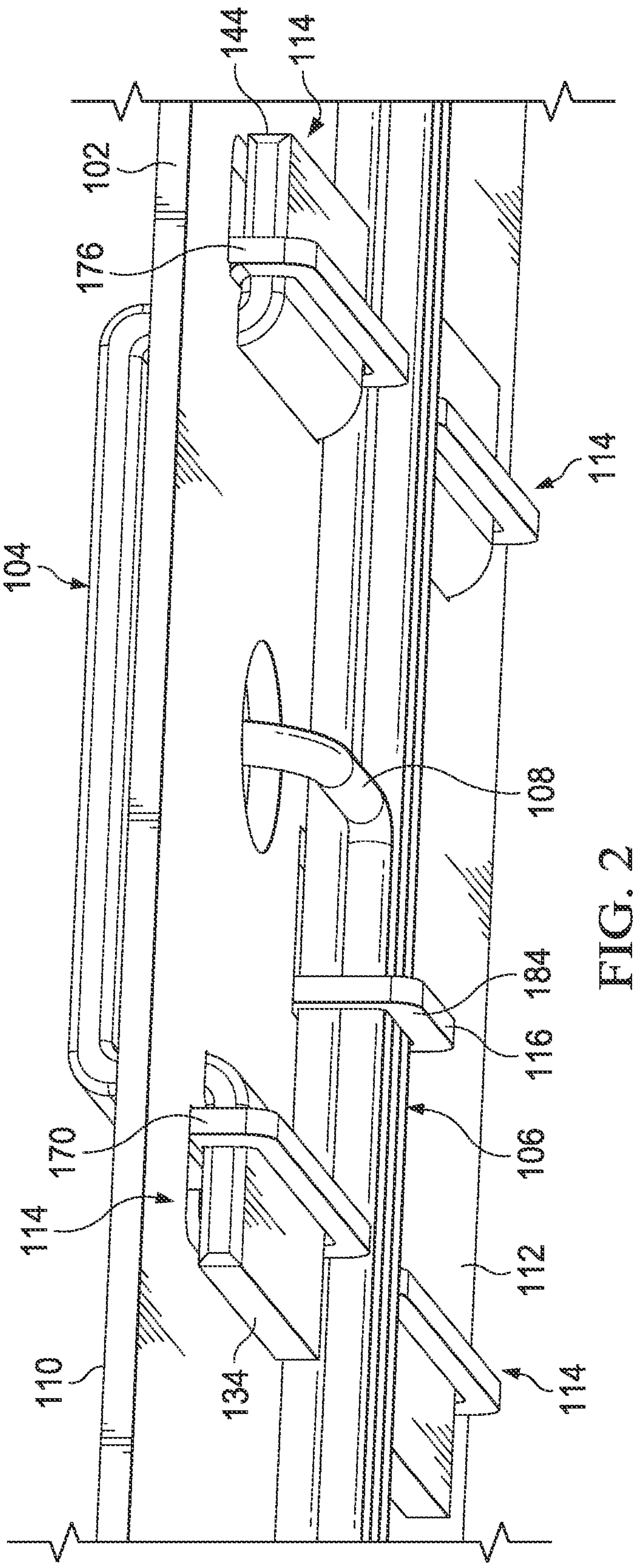
FIG. 2 is a bottom perspective view of a portion of the electrode assembly of FIG. 1 according to embodiments of the present disclosure.
Figure 3:
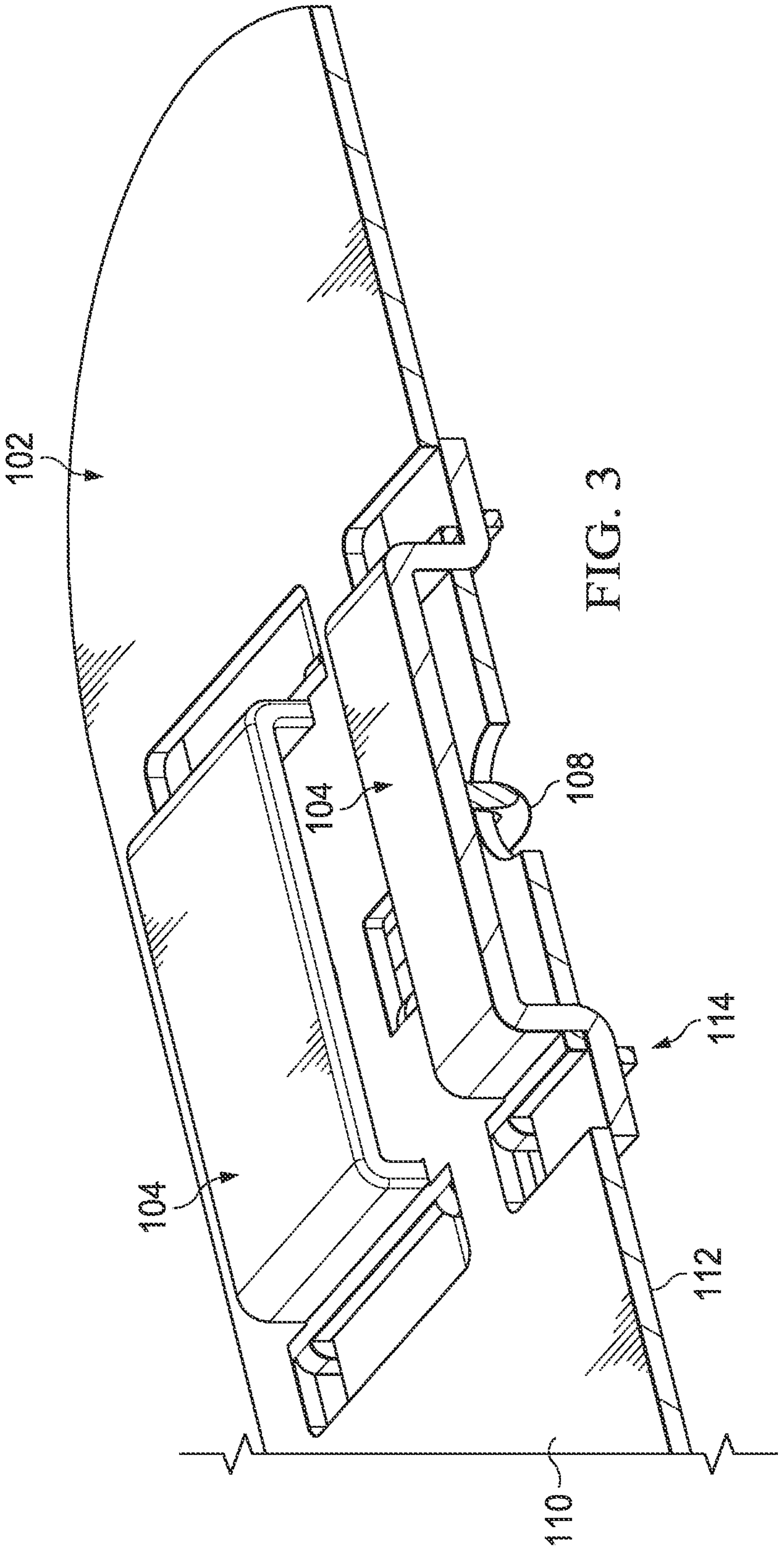
FIG. 3 is a partial sectional view of a portion of the electrode assembly of FIG. 1 according to embodiments of the present disclosure.

FIGS. 1-3 illustrate an example electrode assembly 100 including a substrate 102 and a plurality of electrodes 104 mounted to the substrate 102. Wiring assembly 106 is further mounted to the substrate 102 and is electrically coupled with each of the plurality of electrodes 104. In one embodiment, the wiring assembly 106 is connected to a stimulator configured to independently deliver electrical stimulation to each of the plurality of electrodes 104. To that end, the wiring assembly 106 includes a plurality of wires 108, each wire establishing an electrical connection between the stimulator and an associate electrode 104. As illustrated, each of the plurality of electrodes 104 is positioned on a first side 110 of the substrate 102, whereas the wiring assembly 106 is positioned on a second side 112 of the substrate 102. Any number of electrodes 104 and various arrangements for the electrodes 104 can be used, as desired.

As discussed below, the substrate 102 includes a plurality of electrode connection structures 114 associated with each of the plurality of electrodes 104. The connection structures 114 secure each of the electrodes 104 with respect to the substrate 102 and maintain positioning of the electrodes 104 during manufacturing, assembly and use of the electrode assembly 100. In a similar manner, the substrate 102 further includes a plurality of wiring connection structures 116 that secure the wiring assembly 106 with respect to the substrate and maintains positioning of the wiring assembly 106 with respect to the substrate 102 during manufacturing, assembly and use of the electrode assembly 100.

Figure 4:
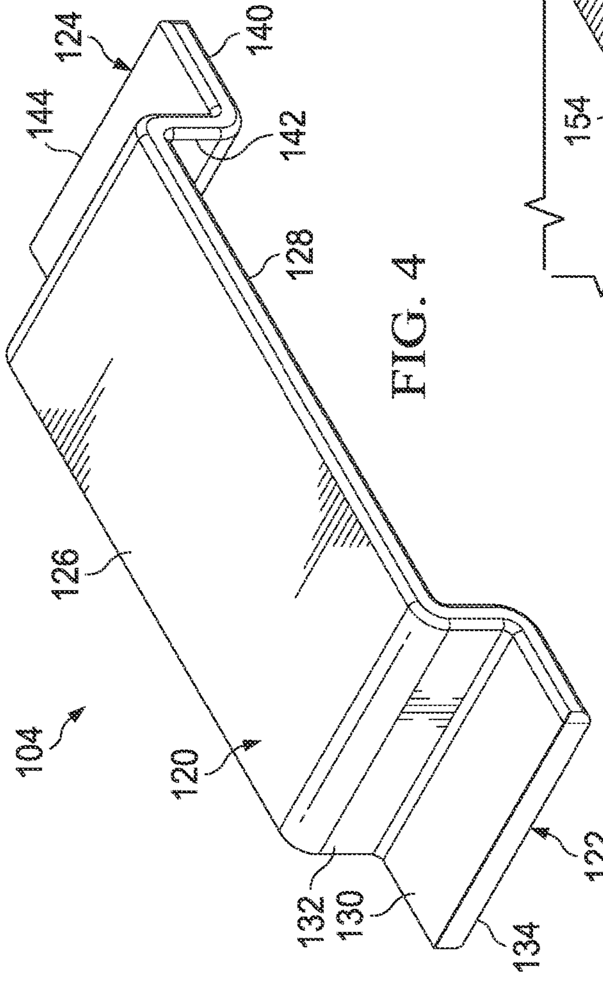
FIG. 4 illustrates a perspective view of an electrode according to embodiments of the present disclosure.

FIG. 4 illustrates an example electrode 104, which can be formed of any conductive material, for example a medical grade alloy such as platinum iridium 90/10, nickel-chromium-cobalt. In one embodiment, the electrode 104 can be formed of elongate strips having a selected width, wherein a machine (e.g., a stamping press) cuts the strip to a desired length as discussed below with respect to FIGS. 26-30. The elongate strips used can be formed with curved or rounded edges to allow handling by persons and preventing cuts from undesired sharp edges. In addition, the machine can form any features of the electrode (e.g., legs, holes) as discussed herein. In other embodiments, the electrodes can be formed of different processes and/or be formed of different shapes. In one example, the electrode can form a dome. In another example, the electrode can include an annular flange that is used to seat against a surface of the substrate.

In the embodiments illustrated, the electrode 104 includes a central portion 120, a first leg portion 122 and a second leg portion 124 positioned on an opposite side of the central portion 120 from the first leg portion 122. The central portion 120 includes a stimulation surface 126 positioned to face away from the substrate 102 and contact the user to deliver stimulation thereto. The stimulation surface 126 is illustrated as generally planar and of a desired surface area to deliver enough stimulation to an area of a patient. Opposite the stimulation surface 126 is a contact surface 128, where contact is made with an associated wire 108 (see FIG. 3). It is worth noting that electrode 104, in one embodiment, is a unitary body (e.g., formed during a stamping procedure) where connection to the electrode 104 can be made at any position on the electrode 104 and not necessarily the contact surface 128.

The first leg portion 122 includes a horizontal portion 130 and a vertical portion 132 connecting the horizontal portion 130 with the central portion 120. The horizontal portion 130 includes an insertion end 134 configured to be coupled with the substrate 102, whereas the vertical portion 132 locates the stimulation surface 126 away from the substrate 102. In a similar manner, the second leg portion 124 includes a horizontal portion 140 and a vertical portion 142. The horizontal portion includes an insertion end 144 configured to be coupled with the substrate 102, whereas the vertical portion 142 locates the stimulation surface away from the substrate 102.

Figure 5:
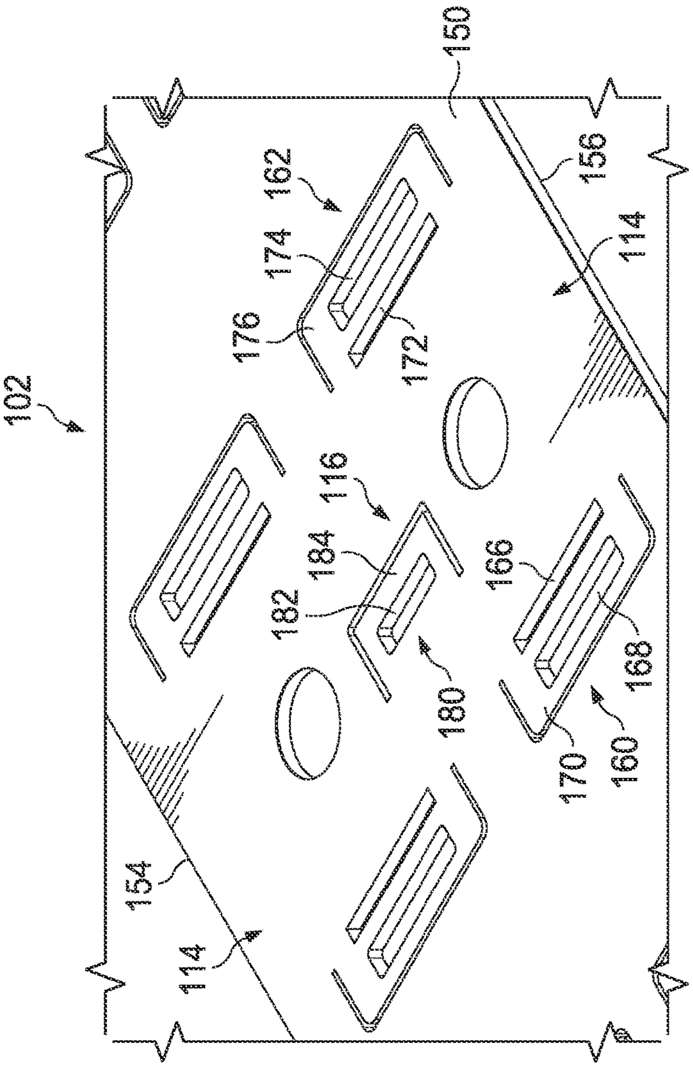
FIG. 5 is a partial perspective view of a substrate during manufacture according to embodiments of the present disclosure.

With reference to FIG. 5, the substrate 102 can be formed of a unitary body 150 defining a perimeter edge with a first, proximal end 154 and a second, distal end 156. In one embodiment, the body 150 can be formed during an independent process than that of formation of the connection structures 114, 116. For example, the body 150 can be formed of an injection molding process with perimeter edge defined after the injection molding process. Alternatively, the body 150 can be formed through a laser cutting process with perimeter edge and connection structures 114, 116 formed in the same laser cutting process. Other methods of forming the body 150 and connection structures 114, 116 are contemplated.

With further reference to FIG. 5, an example electrode connection structure 114 and a wiring assembly connection structure 116 are shown in a close-up view during manufacture of the body 150. Electrode connection structure 114 includes a first tab 160, a second tab 162 opposite the first tab 160 and a central opening 164 positioned between the first tab 160 and the second tab 162. Each of the tabs 160, 162, as well as central opening 164, can be laser cut from the body 150 or otherwise formed using other methods. The first tab 160 defines a first opening 166, a second opening 168 and a tab body 170. In a similar manner, the second tab 162 defines a first opening 172, a second opening 174 and a tab body 176. After formation of the first tab 160, the tab body 170 can be bent downward (i.e., such the tab body extends at an angle) away from substrate 102. Similarly, after formation of the second tab 162, tab body 176 can be bent downward (i.e., such the tab body extends at an angle) away from substrate 102. To mount electrode 104 to substrate 102, insertion end 134 can be inserted through opening 166 and 168 such that leg portion 122 is secured between second side 112 of the substrate 102 and the tab body 170. Similarly, insertion end 144 can be inserted into first opening 172 and opening 174 such that leg portion 124 is secured between second side 112 of the substrate 102 and tab body 176.

Wiring assembly connection structure 116 is formed of a tab 180 including an opening 182 and a tab body 184. The opening 182 and tab body 184 can be formed through a laser cutting process or other suitable method as desired. The tab body 184 can then be bent downward (i.e., such the tab body extends at an angle) away from substrate 102. After tab body 184 is bent downward, wiring assembly 106 can be inserted through opening 182, securing the wiring assembly 106 between the second side 112 of substrate 102 and the tab body 184.

Once the plurality of electrodes 104 and the wiring assembly 106 are mounted to the substrate 102, further manufacturing processes for electrode assembly 100 can commence. For example, each of the wires 108 can be welded to a corresponding electrode 104. Due to registration of the electrodes 104 and the wiring assembly 106 with respect to substrate 102, separation of the electrodes 104 or the wiring assembly 106 with respect to the substrate 102 is reduced and/or prevented. Additionally, the electrode assembly 100 can be subject to an overmolding process, where an insulating material such as silicone is provided to encapsulate substrate 102 while leaving each stimulator surface 126 of electrodes 104 exposed to apply stimulation to a patient.

Figure 6:
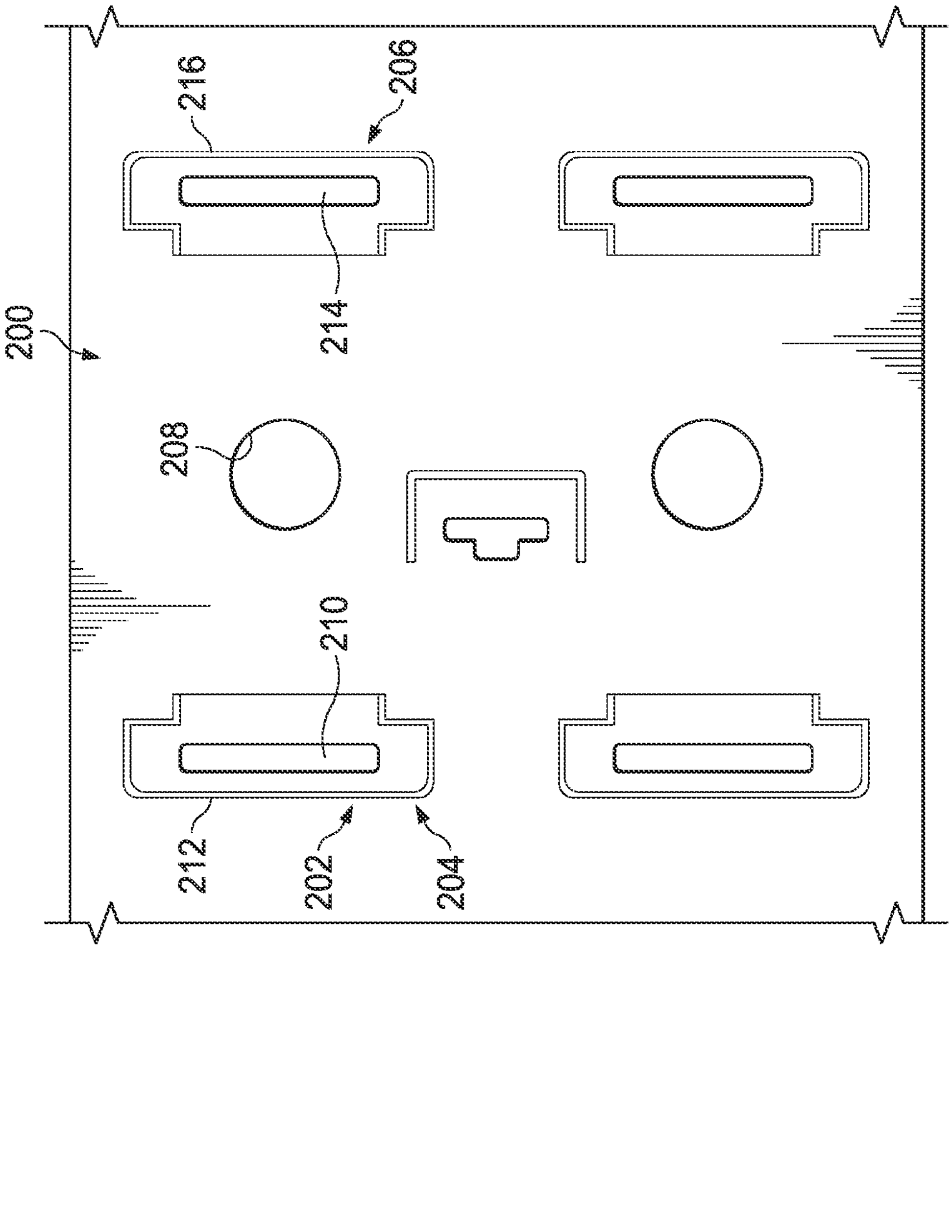
FIG. 6 is a partial plan view of an alternative substrate during manufacture according to embodiments of the present disclosure.
Figure 7:
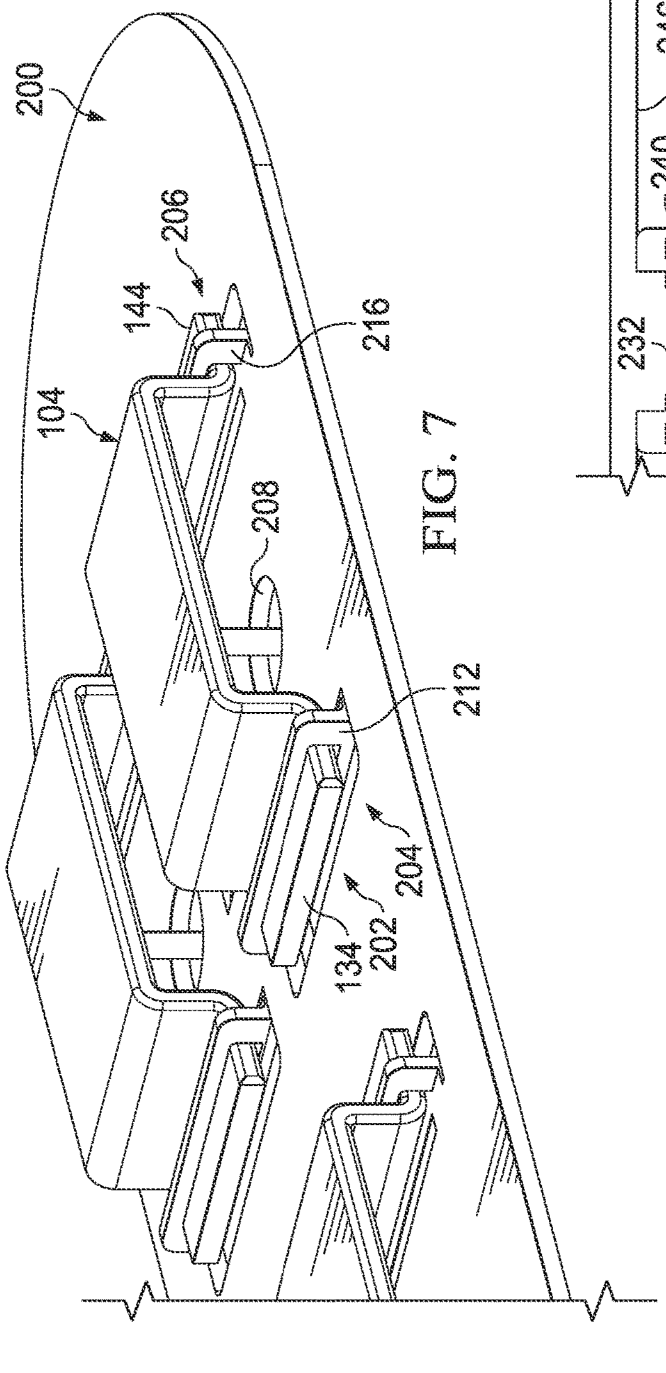
FIG. 7 is a partial perspective view of the substrate of FIG. 6 having electrodes and wiring mounted thereto according to embodiments of the present disclosure.

Those skilled in the art will appreciate that changes can be made to various features of the electrode assembly 100 as will be described below. FIGS. 6 and 7 illustrate an alternative substrate 200 having an electrode connection structure 202. Electrode connection structure 202 includes a first coupling end 204, a second coupling end 206 and a central opening 208 positioned between the first coupling end 204 and the second coupling end 206. The first coupling end 204 includes an opening 210 and a tab body 212. In the embodiment illustrated, tab body 212 is rotated upward and away from substrate 200. Insertion end 134 of electrode 104 can be inserted into the opening 210 such that the insertion end 134 is positioned between substrate 200 and tab body 212. Similarly, second coupling end 206 includes an opening 214 and a tab body 216. To assemble electrode 104 to substrate 200, tab body 216 is rotated upward away from substrate 200 (whereas the tab body 170 in the embodiment of FIGS. 1-5 is bent downward away from substrate 102), thereby allowing insertion end 144 to be inserted through opening 214 such that insertion end 144 is positioned between substrate 200 and tab body 216.

Figure 8:
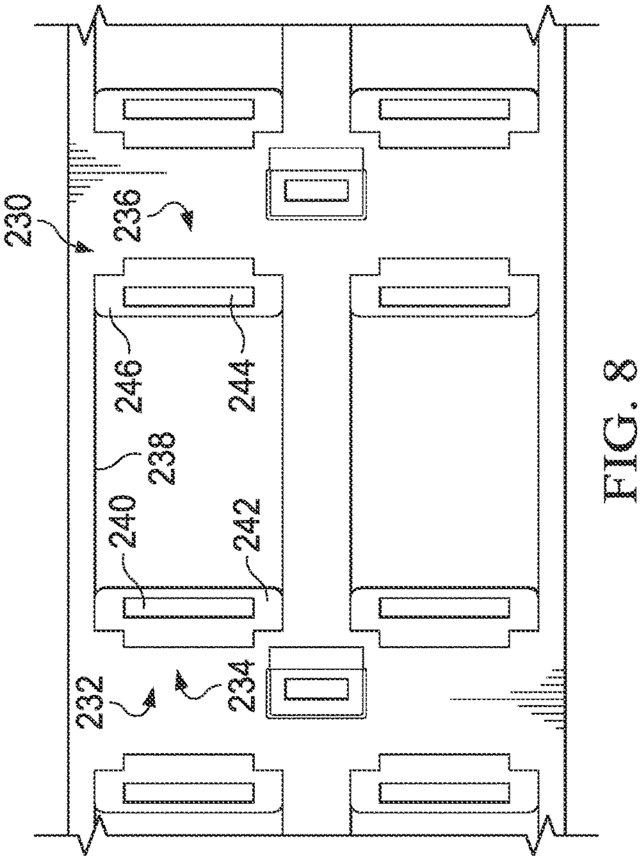
FIG. 8 is a partial plan view of an alternative substrate during manufacture according to embodiments of the present disclosure.
Figure 9:
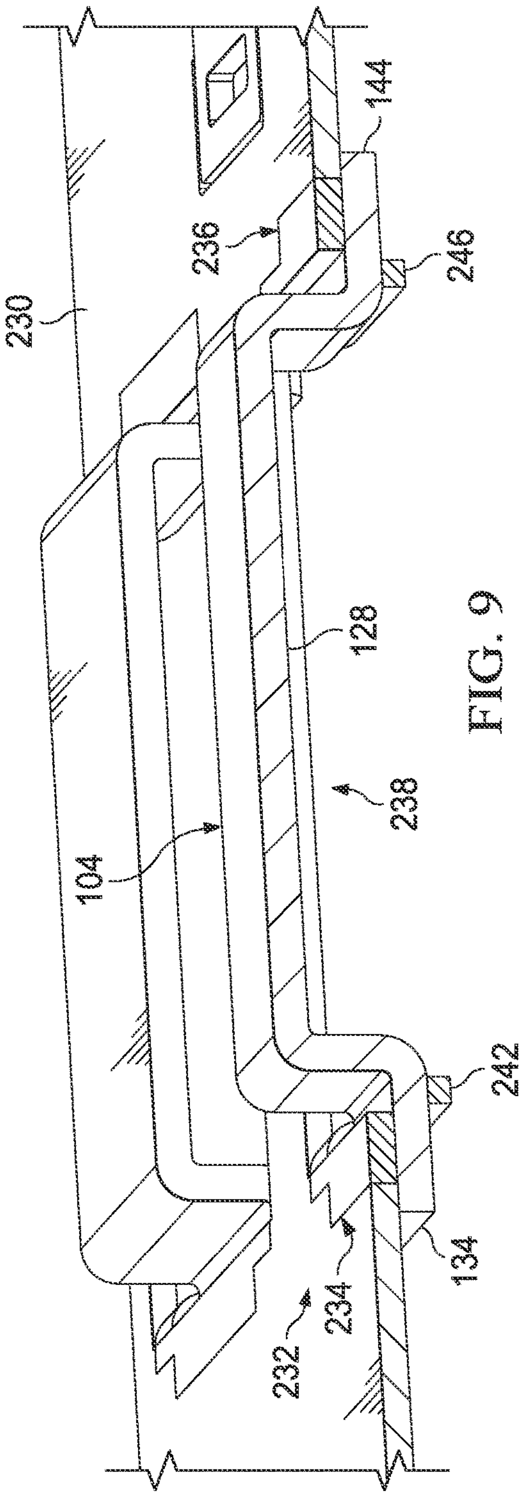
FIG. 9 is a partial perspective view of the substrate of FIG. 8 having electrodes and wiring mounted thereto according to embodiments of the present disclosure.

Another alternative substrate 230 having an electrode connection structure 232 is illustrated in FIGS. 8 and 9. The connection structure 232 includes a first coupling end 234 and a second coupling end 236 positioned on opposite sides of a central opening 238. The first coupling end 234 includes an opening 240 and a tab body 242. To assemble electrode 104 to substrate 230, tab body 242 is rotated downward and away from substrate 230, allowing insertion end 134 to be inserted into opening 240 and positioned between an underside of substrate 230 and tab body 242. Coupling end 236 includes an opening 244 and a tab body 246. To assemble electrode 104 to substrate 230, tab body 246 is rotated downward and away from substrate 230, allowing insertion end 144 to be inserted into opening 244 and positioned between an underside of substrate 230 and tab body 246. Note that in the embodiment of FIGS. 8-9, due to the presence of the central opening 238, no portion of the substrate 230 is located directly below the contact surface 128 of the electrode 104.

Figure 10:
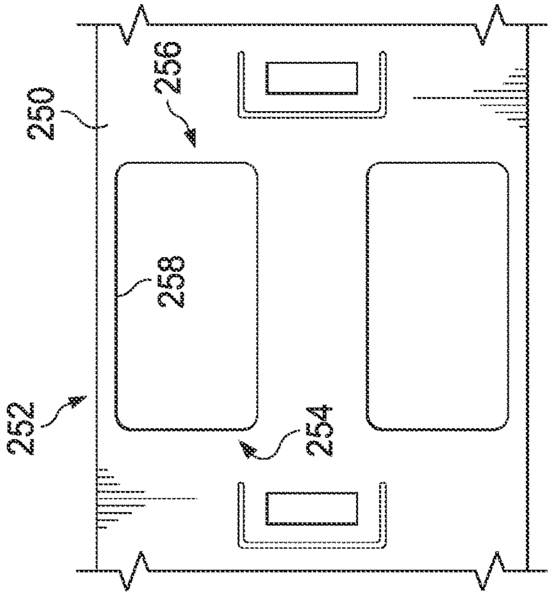
FIG. 10 is a partial plan view of an alternative substrate during manufacture according to embodiments of the present disclosure.
Figure 11:
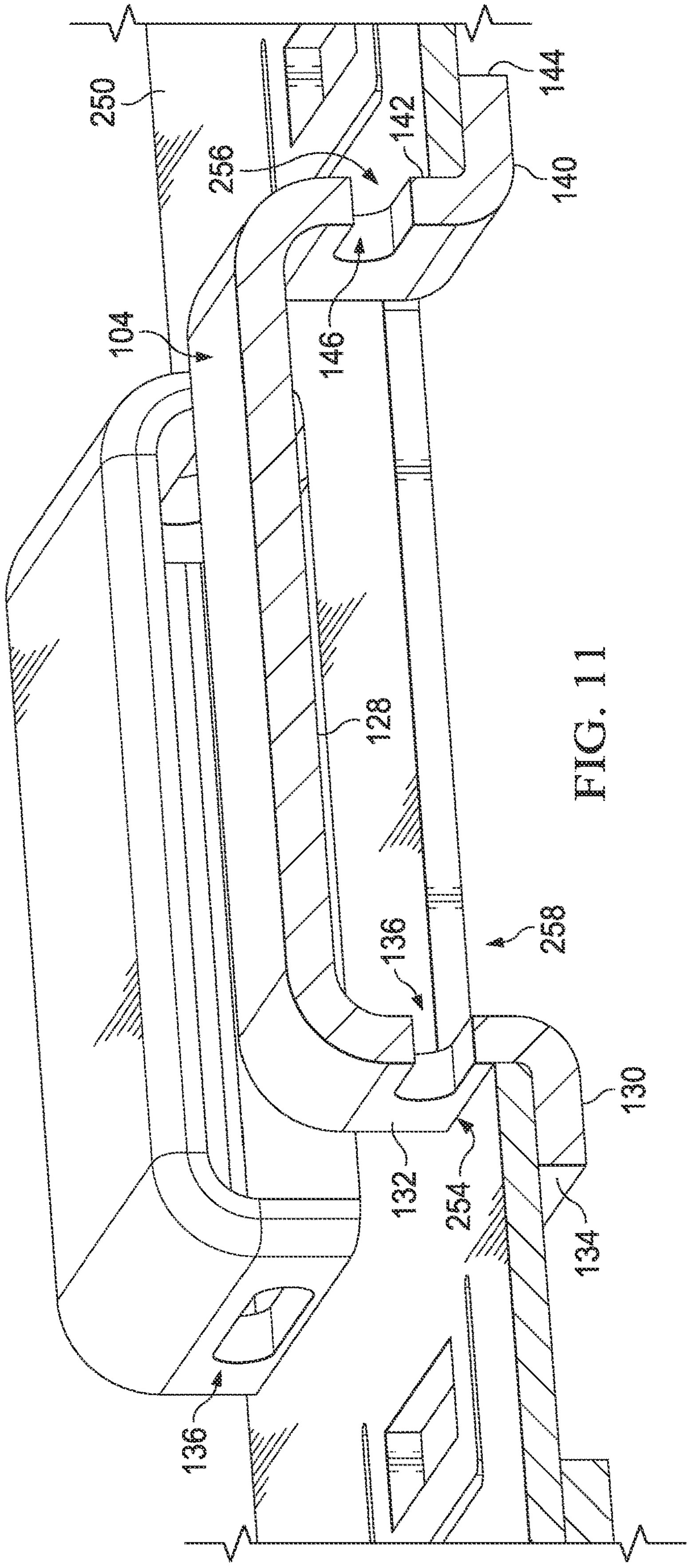
FIG. 11 is a partial perspective view of the substrate of FIG. 10 having electrodes and wiring mounted thereto according to embodiments of the present disclosure.

FIGS. 10 and 11 illustrate another alternative substrate 250, which includes an electrode connection structure 252. The connection structure 252 includes a first coupling end 254 and a second coupling end 256. The first coupling end 254 and second coupling end 256 are positioned on either side of a central opening 258. To assemble electrode 104 to substrate 250, a press or interference fit can be utilized, wherein electrode 104 deflects slightly (e.g., in the horizontal direction) such that vertical portion 132 engages first coupling end 254 and vertical portion 142 engages second coupling end 256, thereby securing electrode 104 within the opening 258. Note that in the embodiment of FIGS. 10-11, no flip-up tabs or flip-down tabs are used to secure the electrode 104 to the substrate 250. Instead, the electrode 104 can be pushed through the central opening 258 (e.g., via the slight deflection of the electrode 104), and the horizontal portions 130 and 140 of the electrode may serve as flanges to "catch" the substrate 250. Again, due to the presence of the central opening 258, no portion of the substrate 250 is located directly below the contact surface 128 of the electrode 104.

Another feature of the electrode 104 of the embodiment shown in FIGS. 10-11 is that openings 136 and 146 (similar to the embodiment of FIG. 4B) are implemented in the vertical side portions of the electrode 104. Silicone or other types of molding materials may be retained within the openings 136 and/or 146. As such, for the electrode 104 to break away from the substrate 250, not only would the legs (e.g., the horizontal portions 130/140) of the electrode be bent, but the molding material in the openings 136 and 146 would also have to tear apart from the rest of the molding material. In this manner, the openings 136 and 146 help promote adhesion between the electrode 104 and the substrate 250.

Figure 12:
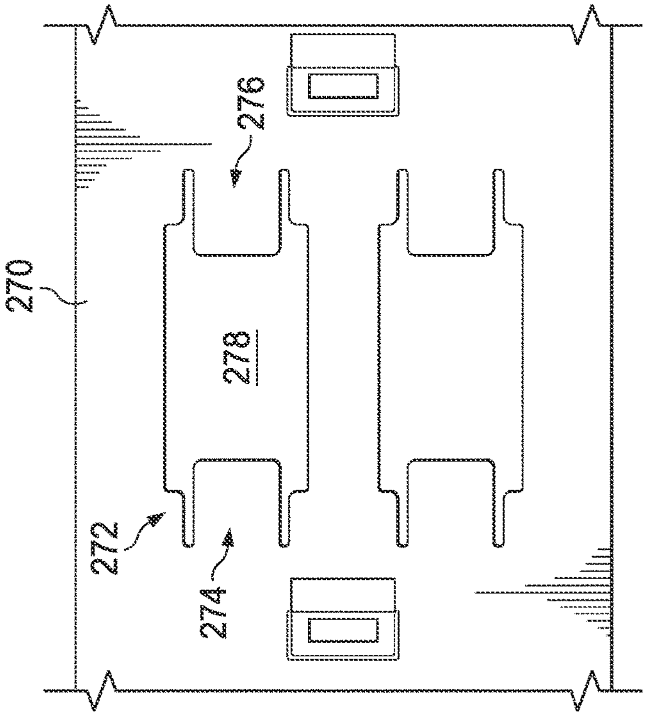
FIG. 12 is a partial plan view of an alternative substrate during manufacture according to embodiments of the present disclosure.
Figure 13:
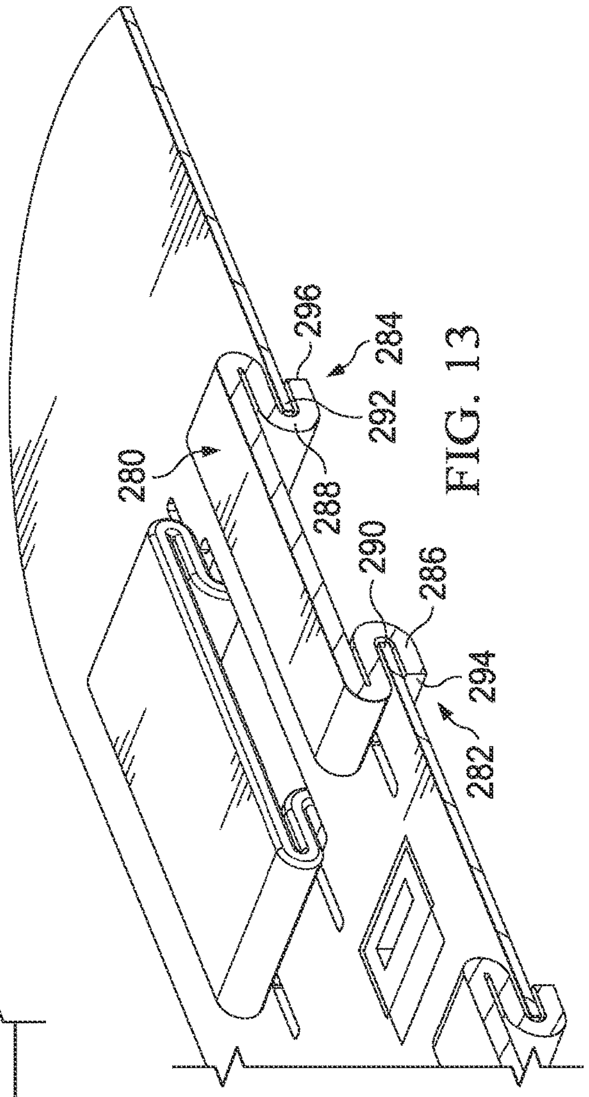
FIG. 13 is a partial perspective view of the substrate of FIG. 12 having electrodes and wiring mounted thereto according to embodiments of the present disclosure.
Figure 14:
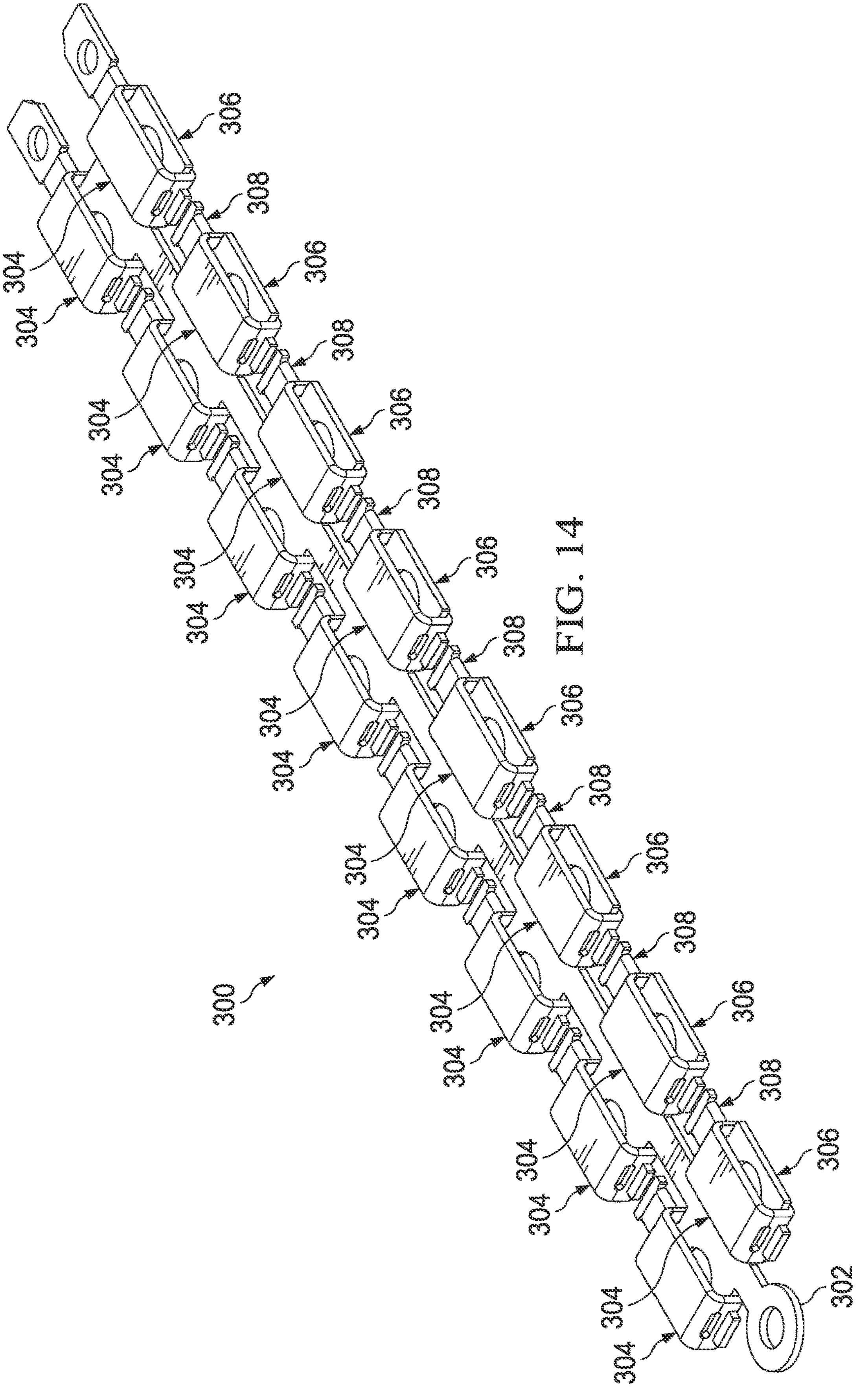
FIG. 14 is a perspective view of an alternative electrode assembly according to embodiments of the present disclosure.
Figure 15:
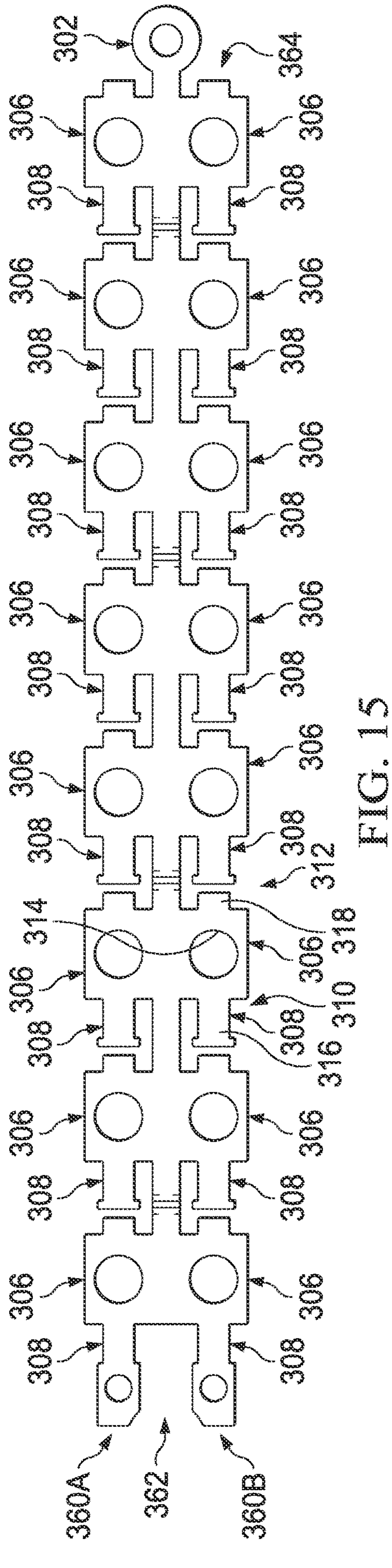
FIG. 15 is a plan view of a substrate of the electrode assembly of FIG. 14 according to embodiments of the present disclosure.
Figure 16:
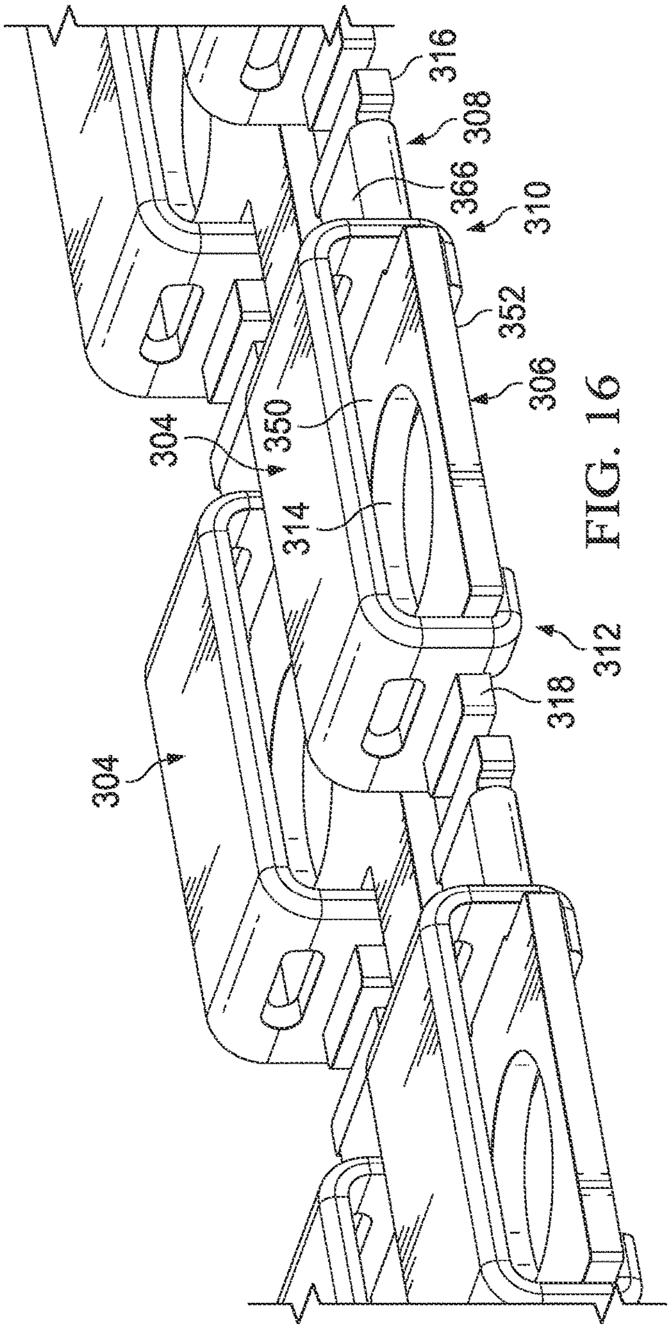
FIG. 16 is a close-up partial perspective view of the electrode assembly of FIG. 14 according to embodiments of the present disclosure.

FIGS. 12 and 13 illustrate another alternative substrate 270, which includes an electrode connection structure 272. The connection structure 272 includes a first coupling end 274 and a second coupling end 276. The first coupling end 274 and second coupling end 276 are positioned on either side of a central opening 278. In this embodiment, an alternative electrode 280 is utilized, which includes a first serpentine leg 282 and a second serpentine leg 284 opposite the first serpentine leg 282. The first serpentine leg 282 forms a notch 286, and the second serpentine leg 284 forms a notch 288. The notch 286 receives a corresponding tab 290, whereas the notch 288 receives a corresponding tab 292. To couple electrode 280 to substrate 270, an insertion end 294 of the first leg 282 can be inserted through opening 278 such that tab 290 registers within notch 286. Likewise, an insertion end 296 of the second leg 284 can be inserted through opening 278 such that tab 292 registers within notch 288. Although not illustrated herein for reasons of simplicity, a wire such as the wire 108 discussed above may be crimped to the electrode 280 (e.g., to the bottom surface of the electrode 280), in order to establish electrical connections between the electrode 280 and other components.

FIGS. 14-17 illustrate an alternative electrode assembly 300. Electrode assembly 300 includes a substrate 302 and a plurality of electrodes 304 mounted to the substrate 302. The substrate 302 includes a plurality of electrode connection structures 306 and a plurality of wiring connection structures 308 extending from each electrode connection structure 306. Each electrode connection structure 306 includes a first coupling end 310, a second coupling end 312 and a central opening 314 positioned between the first coupling end 310 and the second coupling end 312. The first coupling end 310 includes a first tab body 316, and the second coupling end

312 includes a second tab body 318. Electrode 304 is configured to engage the tab body 316 and the tab body 318 to secure electrode 304 to substrate 302.

Similar to electrode 104, electrode 304 can be formed of any conductive material and in particular a medical grade metal alloy such as nickel-chromium-cobalt. The electrode 304 includes a central portion 320, a first leg portion 322 and a second leg portion 324 positioned on an opposite side of the central portion 320 from the first leg portion 322. The central portion 320 includes a stimulation surface 326 positioned to face away from the substrate 302 and contact the user to deliver stimulation thereto. The stimulation surface 326 is illustrated as generally planar and of a desired surface area so as to deliver sufficient stimulation to an area of a patient. Opposite the stimulation surface 326 is a contact surface 328, where contact is made with an associated wire (e.g., the wire 108 discussed above). It is worth noting that electrode 304, in one embodiment, is a unitary body where connection to the electrode 304 can be made at any position on the electrode 304 and not necessarily the contact surface 328.

The first leg portion 322 includes horizontal projections 330A, 330B and a vertical portion 332 connecting the horizontal projections 330A, 330B with the central portion 320. The horizontal projections 330A, 330B define an opening 334 configured to be coupled with the tab body 316 of the substrate 302, whereas the vertical portion 332 locates the stimulation surface 326 away from the substrate 302. In a similar manner, the second leg portion 324 includes horizontal projections 340A, 340B and a vertical portion 342. The horizontal projections 340A, 340B define an opening 344 configured to be coupled with the tab body 318 of substrate 302, whereas the vertical portion 342 locates the stimulation surface 326 away from the substrate 302.

Upon assembly, horizontal projections 330A, 330B, 340A, 340B are positioned on a first side 350 of substrate 302, whereas central portion 320 is positioned on a second side 352 of the substrate 302. A wiring assembly (not shown) can extend linearly along substrate 302 in two columns 360A, 360B, each column extending from a first end 362 of the substrate 302 to a second end 364 of the substrate 302. The wiring assembly can be coupled with each tab body 316 using a suitable attachment mechanism 366. In the embodiment illustrated, the attachment mechanism 366 is a silicone band that wraps around the wiring assembly and tab body 318, although other forms of attachment can also be utilized. In any event, individual wires of the wiring assembly can be threaded through the attachment mechanism 366 and terminate through each respective opening 314 to connect with a respective contact surface 328 of an electrode 304.

One unique characteristic of the electrode assembly 300 of the embodiment illustrated in FIGS. 14-17 is that the electrodes 304 do not pass through the substrate 302. Instead, the electrodes 304 each go around the substrate 302. Portions of the electrodes 304 hug the outer portions of the substrate 302, but the substrate 302 itself does not circumferentially support or hold the electrodes 304.

Figure 18:
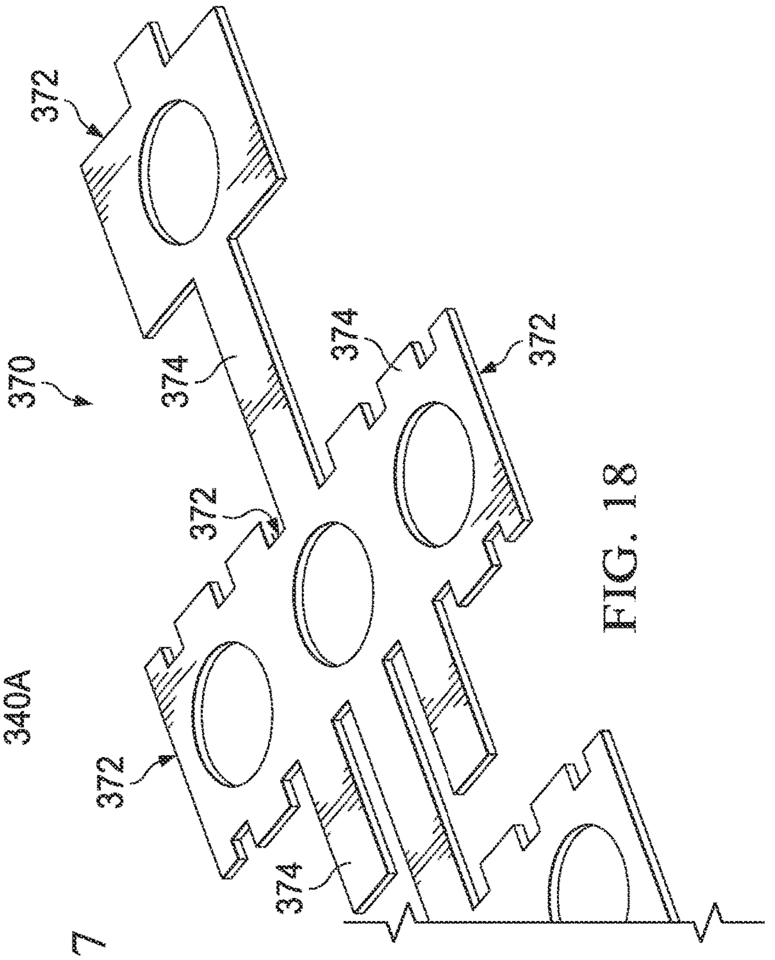
FIG. 18 is a perspective view of an alternative substrate for use in an electrode assembly according to embodiments of the present disclosure.
Figure 17:
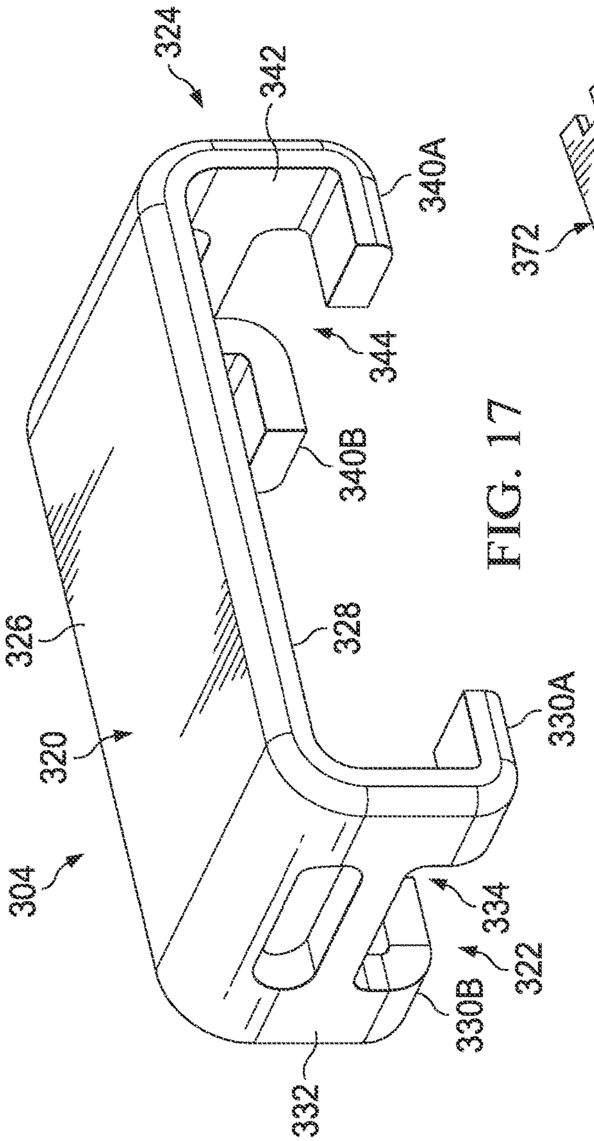
FIG. 17 is a perspective view of an electrode of the electrode assembly of FIG. 14 according to embodiments of the present disclosure.
Figure 19:
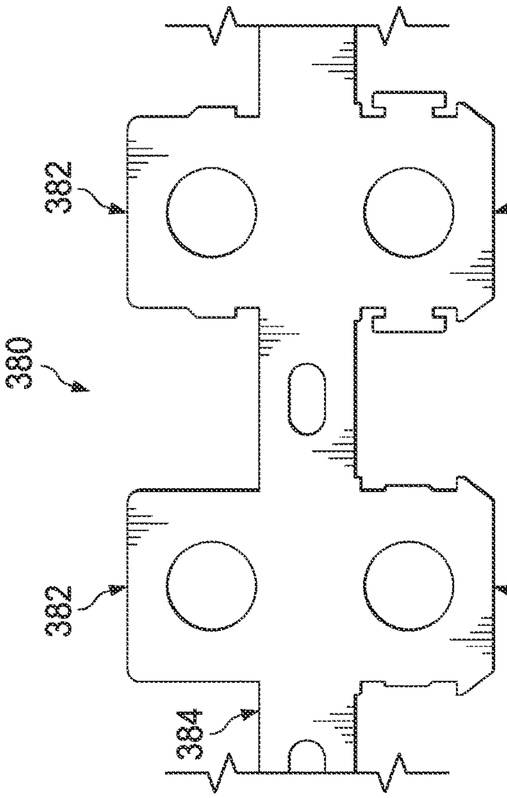
FIG. 19 is a plan view of an alternative substrate for use in an electrode assembly according to embodiments of the present disclosure.
Figure 20:
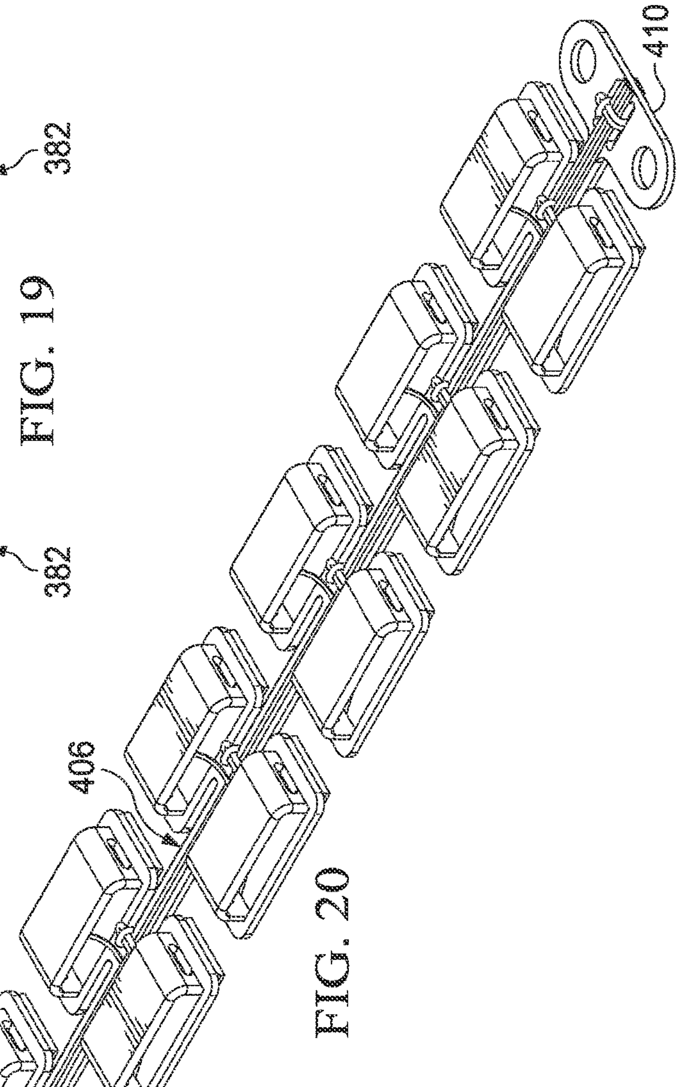
FIG. 20 is a top perspective view of an alternative electrode assembly having a plurality of electrodes coupled with a substrate according to embodiments of the present disclosure.
Figure 20:
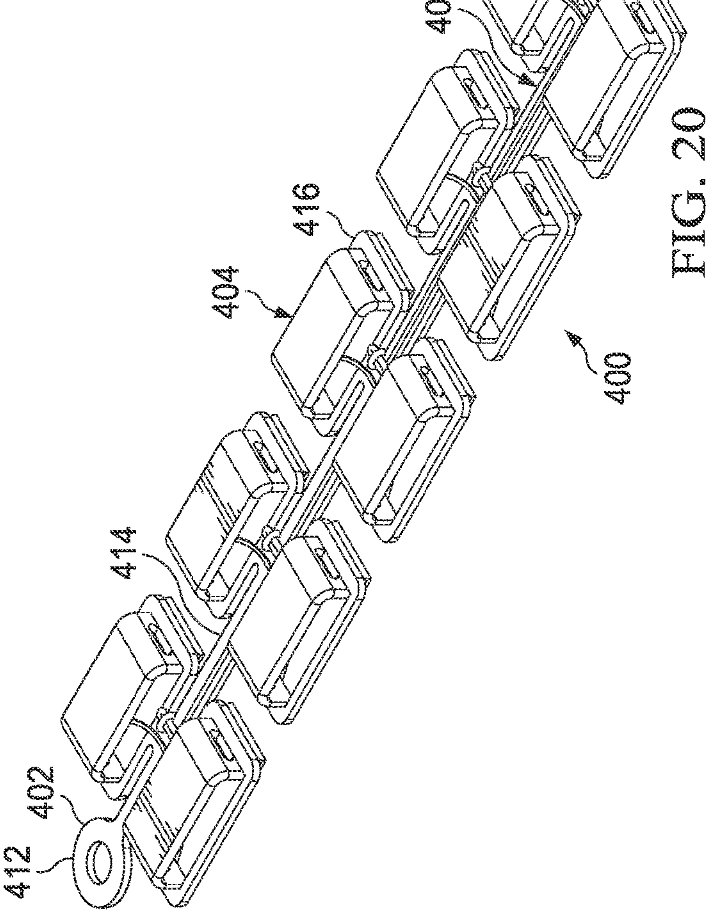

Alternative substrates to substrate 302 can also be utilized, as desired. FIGS. 18 and 19 illustrate alternative substrates 370 and 380, respectively. Substrate 370 includes a plurality of electrode connection structures 372 that are similar in form to connection structures 306 and configured to secure electrodes 304 thereto. In addition, substrate 370 includes a plurality of wiring assembly connection structures 374, each of the connection structures 374 arranged in different columns. Substrate 380 further includes a plurality of electrode connection structures 382 with a single wiring assembly connection structure 384 positioned along a length of the substrate 380.

FIGS. 20-25 illustrates yet another embodiment of an electrode assembly 400, including a substrate 402, a plurality of electrodes 404 and a wiring assembly 406. The substrate 402 extends from a first, proximal end 410 to a second, distal end 412. An elongate stem portion 414 and a plurality of individual electrode support structures 416 extending from the stem portion 414 to support the plurality of electrodes 404 therein. The stem portion 414 is centrally located between adjacent ones of the electrode support structures 416 and supports the wiring assembly 406.

Figure 21:
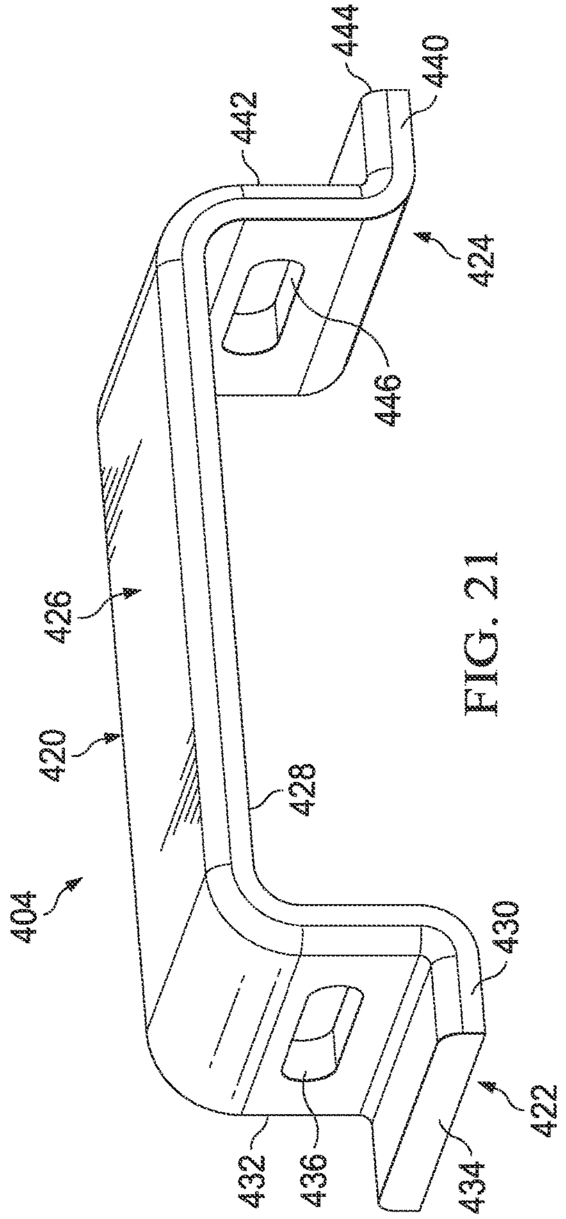
FIG. 21 is a perspective view of an electrode used in the electrode assembly of FIG. 20 according to embodiments of the present disclosure.

As illustrated in FIG. 21, the electrode 404 includes a central portion 420, a first leg portion 422 and a second leg portion 424 positioned on an opposite side of the central portion 420 from the first leg portion 422. The central portion 420 includes a major stimulation surface 426 positioned to face away from the substrate 402 and contact the user to deliver stimulation thereto. The stimulation surface 426 is illustrated as generally planar and of a desired surface area to deliver enough stimulation to an area of a patient. Opposite the stimulation surface 426 is a contact surface 428, where contact is made with an associated wire. It is worth noting that electrode 404, in one embodiment, is a unitary body (e.g., formed during a stamping procedure) where connection to the electrode 404 can be made at any position on the electrode 404 and not necessarily the contact surface 428.

The first leg portion 422 includes a horizontal portion 430 and a vertical portion 432 connecting the horizontal portion 430 with the central portion 420. The horizontal portion 430 includes an insertion end 434 configured to be coupled with the substrate 402, whereas the vertical portion 432 locates the stimulation surface 426 away from the substrate 402. An aperture 436 is positioned in the vertical portion 432. In a similar manner, the second leg portion 424 includes a horizontal portion 440 and a vertical portion 442. The horizontal portion includes an insertion end 444 configured to be coupled with the substrate 402, whereas the vertical portion 442 locates the stimulation surface 426 away from the substrate 402. An aperture 446 is positioned in the vertical portion 442.

Figure 22:
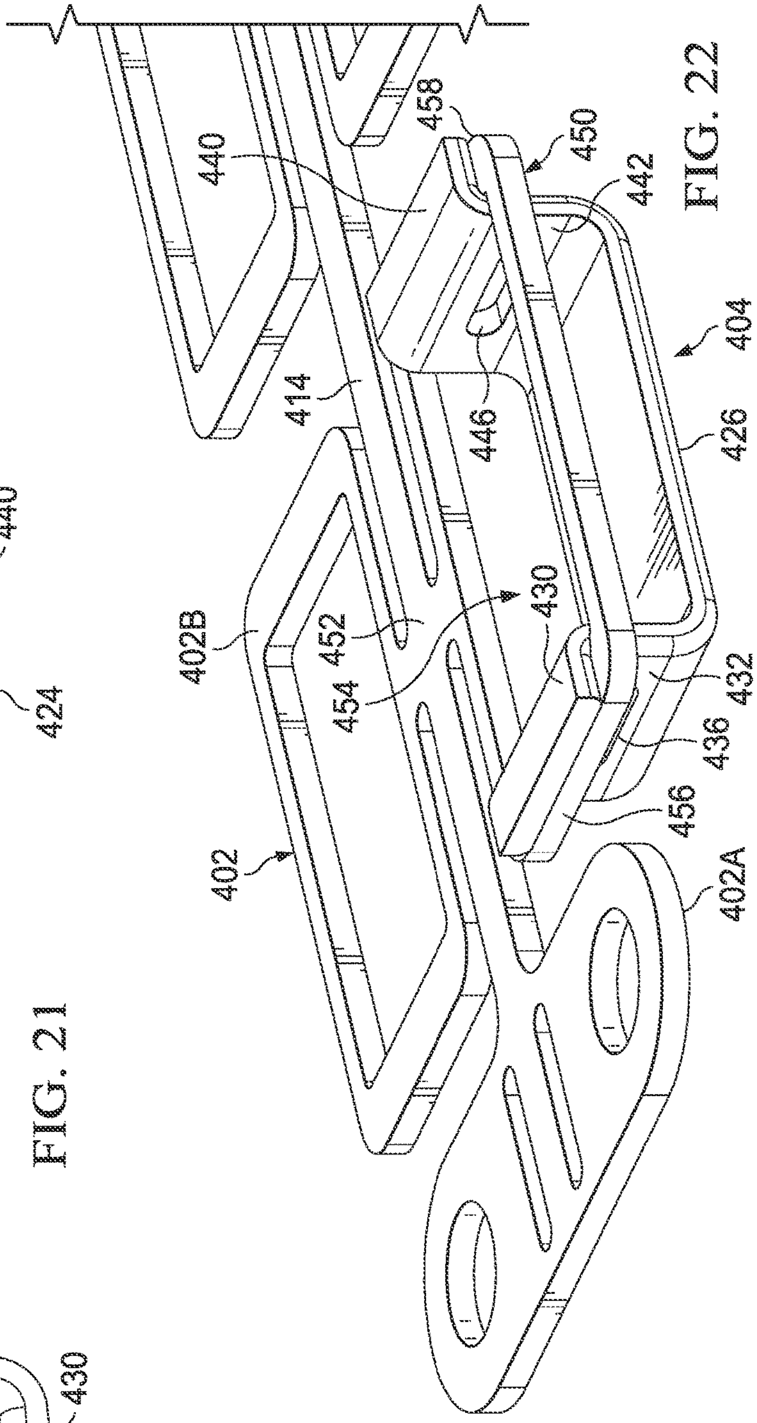
FIG. 22 is a bottom perspective view of the electrode of FIG. 21 positioned within the substrate of FIG. 20 according to embodiments of the present disclosure.
Figure 23:
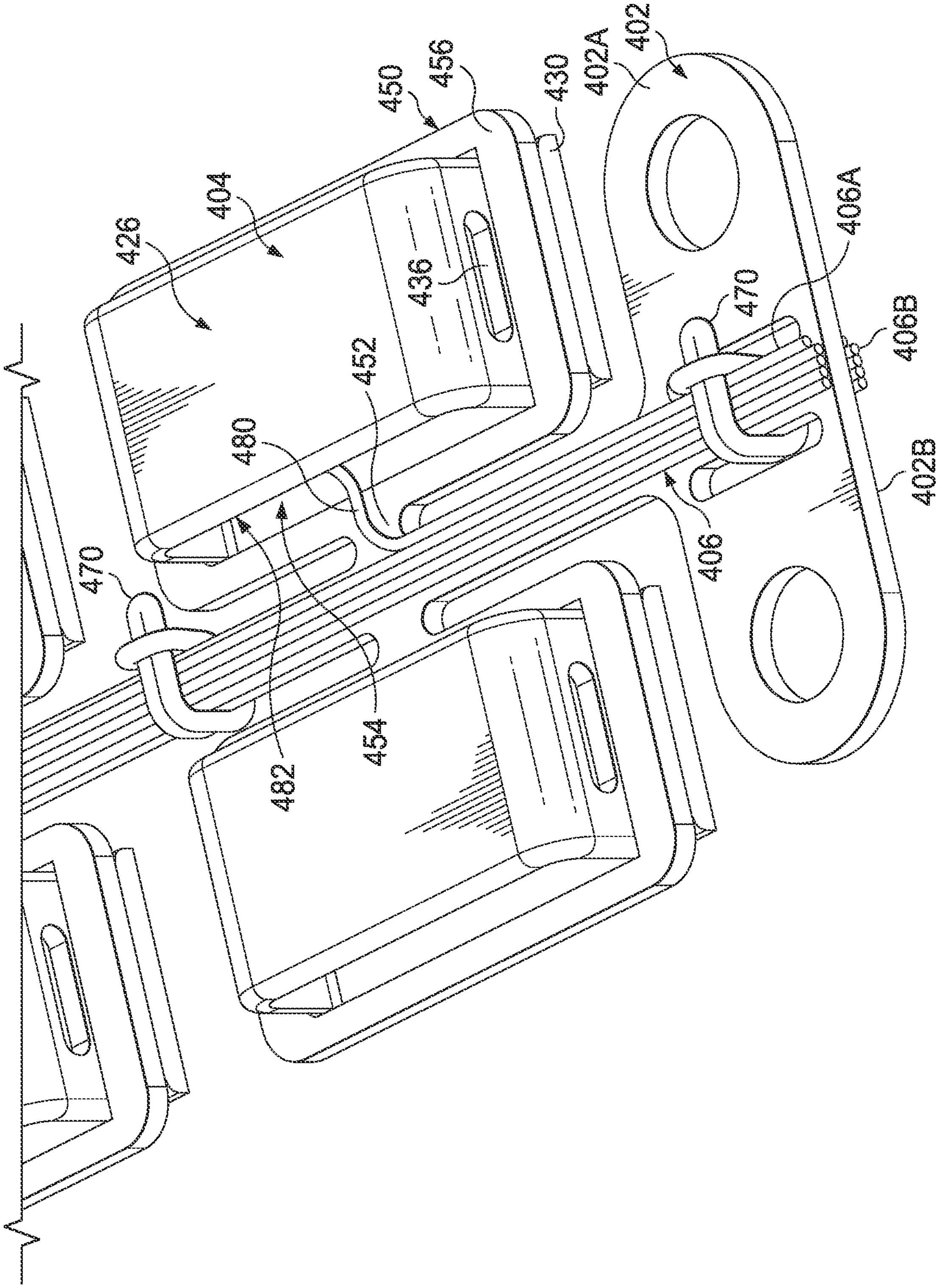
FIG. 23 is a top perspective view of connection of a wire to an electrode according to embodiments of the present disclosure.

To produce assembly 400, each of the plurality of electrodes 404 is positioned in the substrate 402. As illustrated in FIGS. 22 and 23, electrode 404 is inserted into a corresponding electrode connection structure 450 from a bottom surface 402B of the substrate 402. Electrode connection structure 450 is connected with stem portion 414 through a bridge portion 452 and defines an opening 454 having a first coupling end 456 and a second coupling end 458 spaced apart from the first coupling end 456. Although illustrated as generally rectangular, the opening 454 can have any shape as desired. The coupling ends 456 and 458 each establishes a connection point with the electrode 404 to facilitate a press or interference fit between the electrode 404 and the electrode connection structure 450. In particular, the electrode 404 establishes a press or interference fit between at least a first position and a second position on the electrode connection structure 450.

During assembly, the stimulation surface 426 is faced toward the opening 454 on the bottom surface 402B and inserted through the opening 454 until horizontal portions 430 and 440 contact coupling ends 456 and 458, respectively. Electrode 404 and electrode connection structure 450 are sized to cooperate with one another to establish an interference fit upon insertion such that the electrode 404 can be secured to the substrate 402 while wiring is connected to the electrode 404 and an overmold is applied to the assembly 400. In the embodiment illustrated, a distance between vertical portions 432 and 442 is selected such that coupling ends 456 and 458 engage and hold the electrode 404 during further manufacturing processes such as wiring connection and overmolding. After insertion of electrode 404, apertures 436 and 446 are exposed above a top surface 402A of the substrate 402. As a result, overmolding material (e.g., silicone) can enter through the apertures 436 and 446, which assists in securing electrodes 404 in place after the overmolding material has cured.

In order to electrically connect a stimulation source to each electrode 404, wiring assembly 406 includes a plurality of individual wires. In particular, the wiring assembly 406 includes one respective wire for each electrode 404 in assembly 400. With reference to FIG. 23, wiring assembly 406 can be positioned on either side of substrate 402. For example, wiring assembly 406 can include a first wiring bundle 406A positioned on a first side of substrate 402 and a second wiring bundle 406B positioned on a second side of substrate 402. Each individual wire is insulated along its length to prevent electrical connection with adjacent wires. Wiring assembly 406 can be secured to substrate 402 with one or more bands 470 spaced apart along the stem portion 414. In the illustrated embodiment, bands 470 are secured to the substrate 402 using a girth hitch, although other knots and other forms of securing wiring assembly 406 to substrate 402 can be used. For example, bands 470 can be sutures. Other mechanisms can further be employed.

Figure 24:
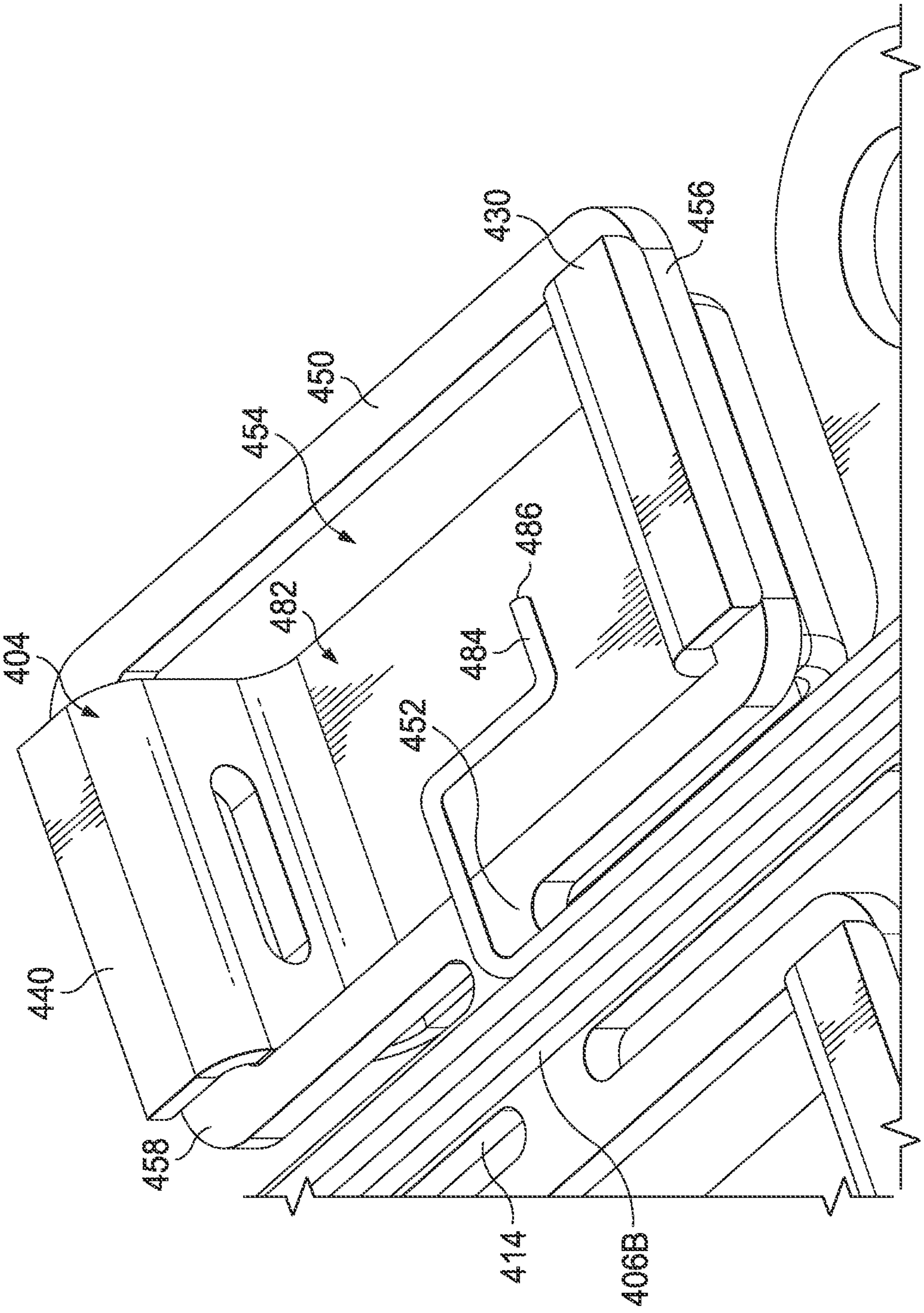
FIG. 24 is a bottom perspective view of connection of a wire to an electrode at a first position according to embodiments of the present disclosure.
Figure 25:
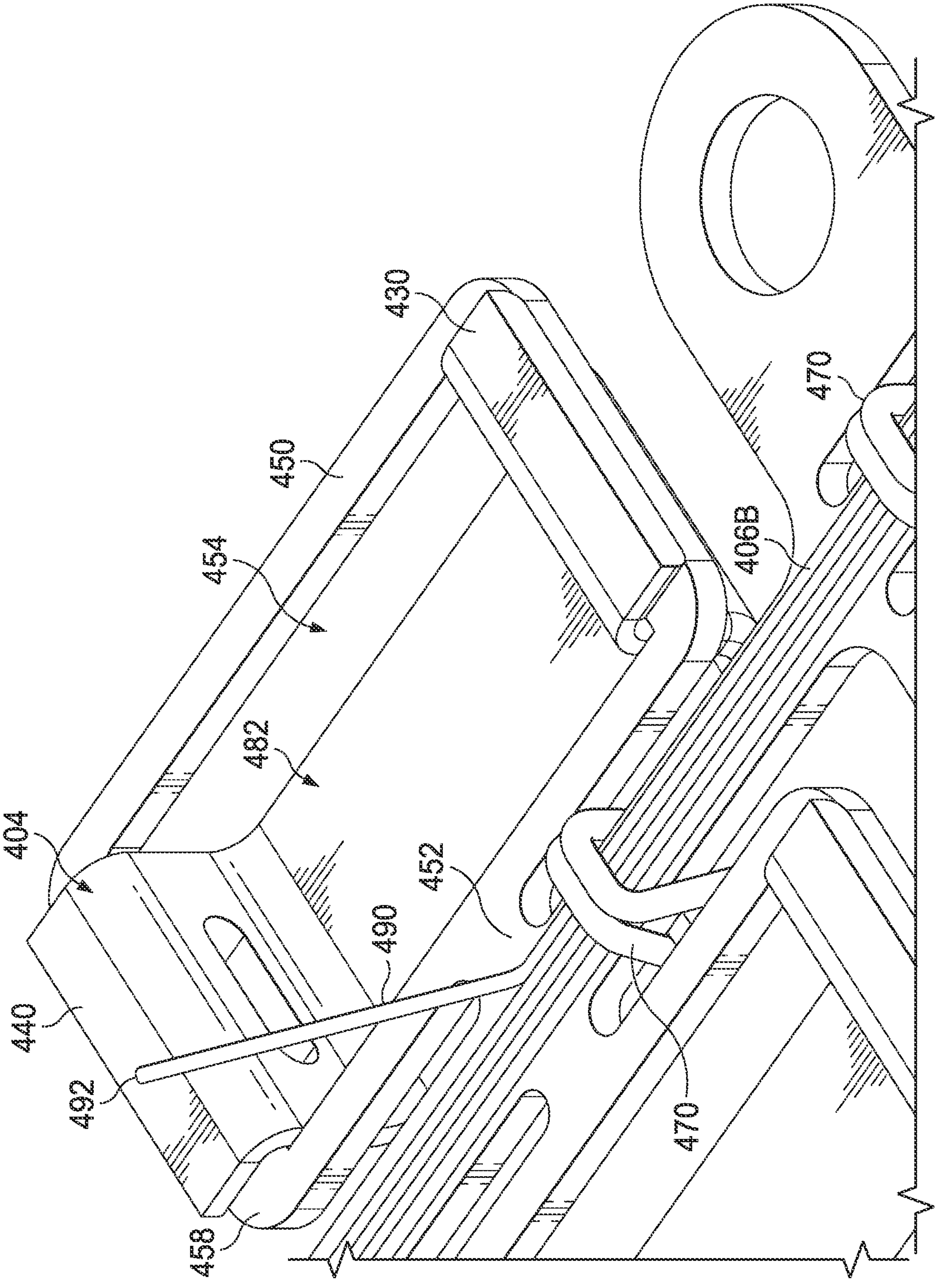
FIG. 25 is a bottom perspective view of connection of a wire to an electrode at a second position according to embodiments of the present disclosure.

Individual wires can be connected to electrodes 404 in various ways. For example, in FIG. 23, an individual wire 480 (part of wiring bundle 406A) extends along bridge portion 452 to an underside surface 482 of electrode 404. In one embodiment, the individual wire 480 is welded to the underside surface 482 to establish electrical connection between the wire 480 and the electrode 404. Other arrangements to establish electrical connection between individual wires of the wiring assembly 406 and electrodes 404 can be used. For example, FIG. 24 illustrates an individual wire 484 as part of wiring bundle 406B and electrically connected with electrode 404 on underside surface 482 at a centrally located position 486. In another embodiment, as illustrated in FIG. 25, an individual wire 490 as part of wiring bundle 406B is electrically connected with electrode 404 on underside surface 482 at a position 492 that is part of horizontal portion 440.

After electrical connection between wiring assembly 406 and each of the plurality of electrodes 404 is made, an overmold material (e.g., silicone) can be applied to assembly 400. The overmold material secures the electrodes 404 to respective ones of the plurality of electrode support structures 416 and secures individual wires of the wiring assembly 406 to the substrate 402 and to the individual electrodes 404.

One of the unique physical characteristics distinguishing the embodiment of the electrode assembly 400 from the conventional electrode assemblies is that no portion of the substrate 402 is located underneath the contact surfaces 428 of the electrodes 404. Such a design improves the performance and reliability of the electrode assembly 400. In more detail, conventional substrates (where portions thereof are typically disposed below the electrodes) may be very thin. The thinness of the substrate may lead to difficulties in performing certain mechanical processes such as press fitting to fit the electrodes on such a thin substrate, since these mechanical processes may inadvertently deform the thin substrate. As such, it may be desirable to thicken the substrate (e.g., in a vertical or Z-direction) to prevent the substrate from being damaged by the mechanical processes such as press fitting. Unfortunately, thickening the substrate may render the substrate too rigid or stiff, which means that the substrate may not be sufficiently pliable when the electrode assembly is implanted inside a patient's body. This could cause patient discomfort and/or lead to degradations in the efficacy of the stimulation therapy delivered by the electrodes. In addition, the molding material (e.g., silicone) of the electrode assembly may move around, and the substrate itself may move and push toward the surface of the electrodes.

To solve these problems associated with conventional electrode assemblies discussed above, FIGS. 21-25 of the present disclosure implements an embodiment where much of the surface area of the substrate 402 has been eliminated, which allows the substrate 402 to be thicker than otherwise suitable. In other words, by eliminating the portions of the substrate 402 underneath the contact surfaces 428 of the electrodes 404, the remaining portion of the substrate 402 is much smaller than conventional substrates (e.g., in terms of total mass or volume). This reduction in surface area of the substrate 402 allows the substrate 402 to be made thicker, such that it can tolerate the mechanical processes such as press fitting without being deformed. Meanwhile, due to the reduction of a substantial amount of surface area, the thickened substrate 402 still maintains sufficient pliability and/or flexibility to not cause problems inside a patient's body.

Figure 26:
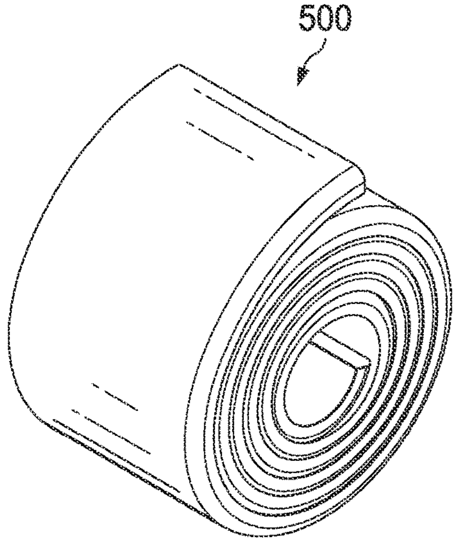
FIGS. 26-30 are successive views of steps in forming an exemplary electrode according to embodiments of the present disclosure.
Figure 27:
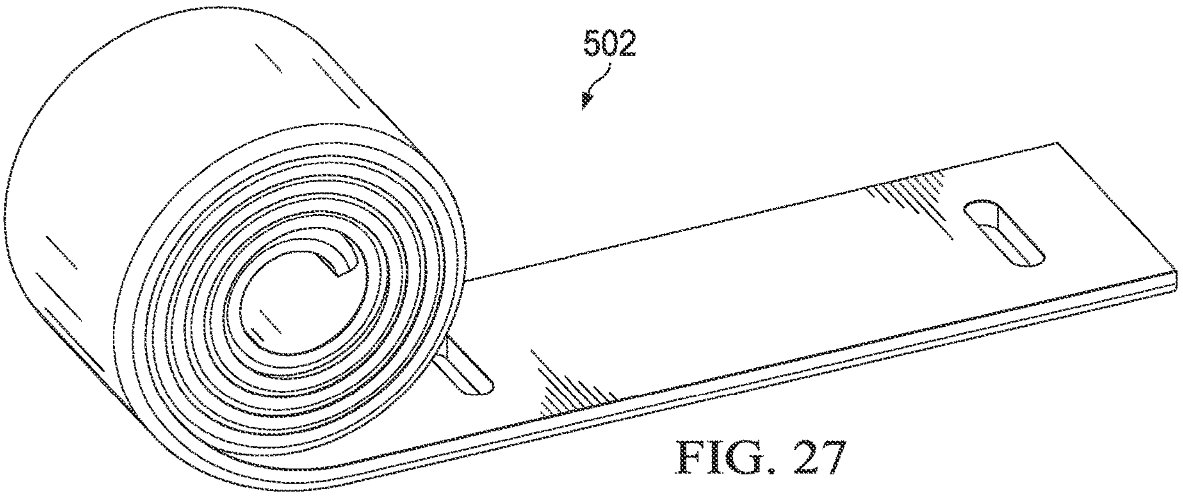
Figure 28:
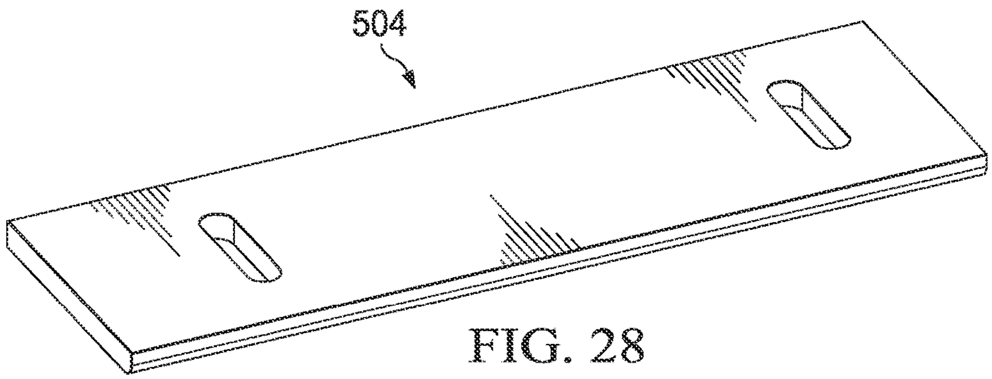
Figure 29:
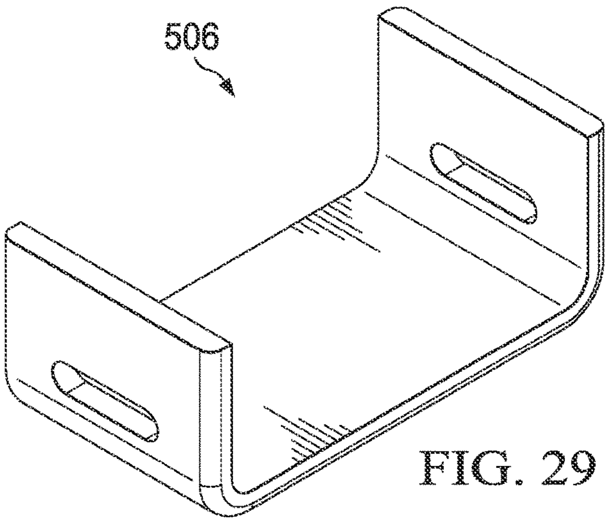
Figure 30:
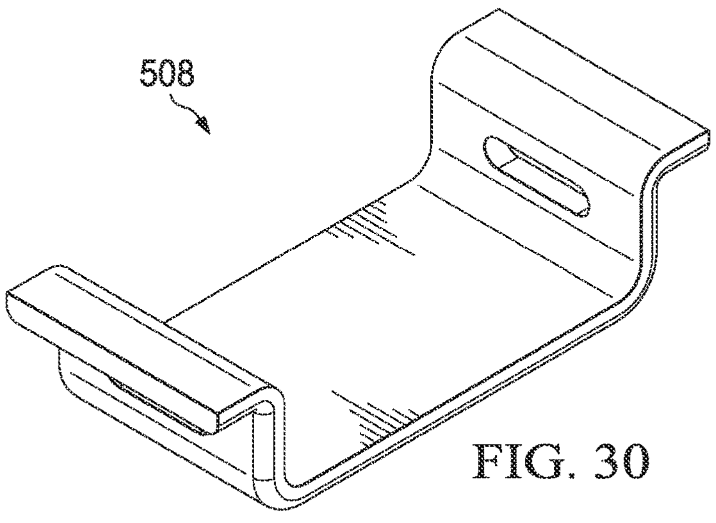

FIGS. 26-30 illustrate successive steps in forming electrodes as described herein. FIG. 26 illustrates a step 500 showing a roll formed of a desired metal alloy having rolled edges. In one example manufacturing process, the step 500 can include forming the roll at a first location and sent to a second location for further processing. As illustrated in FIG. 27, a step 502 is illustrated, wherein the roll is positioned in a stamping machine that unwinds the roll and forms apertures therein. In FIG. 28, a step 504 includes cutting the strip to form an electrode blank with apertures formed therein. Subsequently, as illustrated in FIG. 29, step 506 bends the blank to form opposed legs. In step 508 of FIG. 30, horizontal portions are formed to produce a final electrode.

Figure 31:
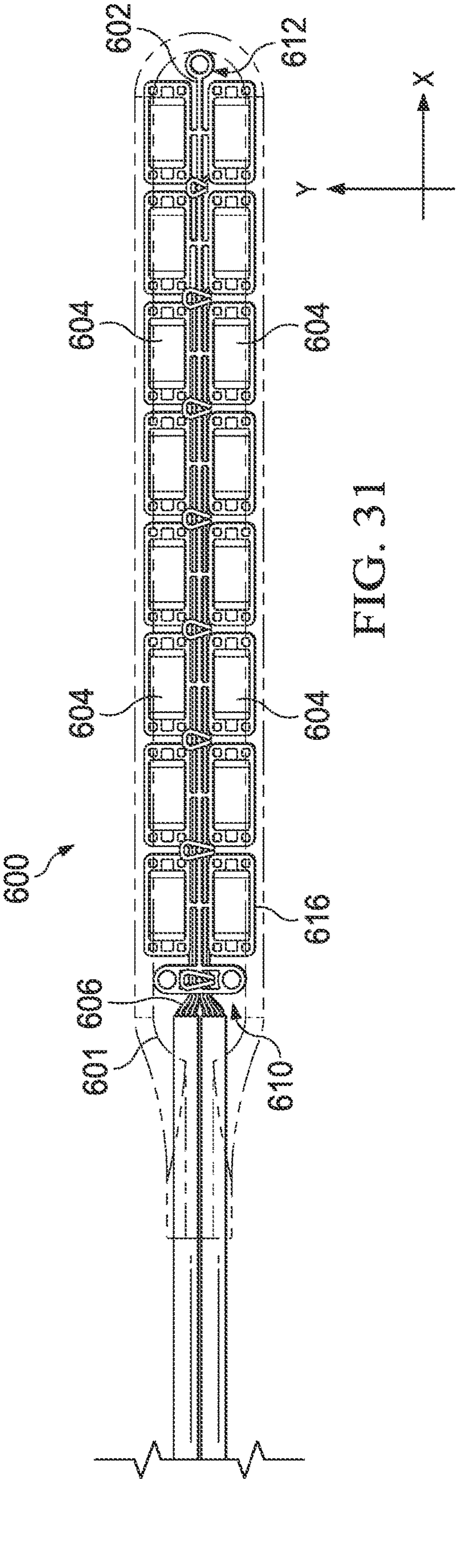
FIGS. 31-48 are three-dimensional perspective views of an electrode assembly according to embodiments of the present disclosure.
Figure 32:
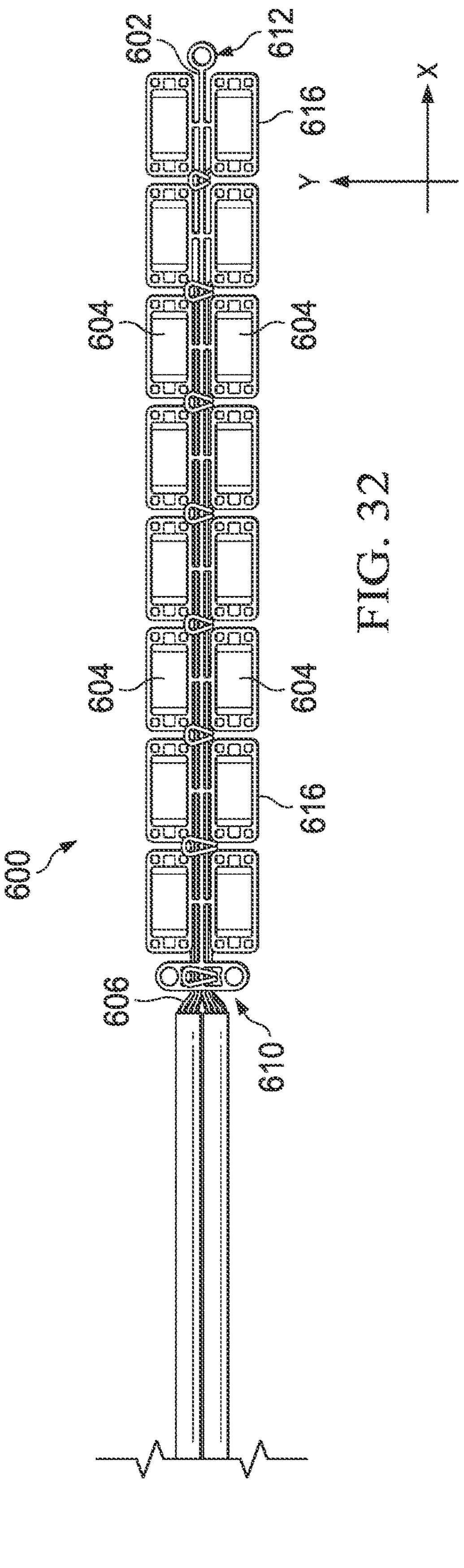
Figure 33:
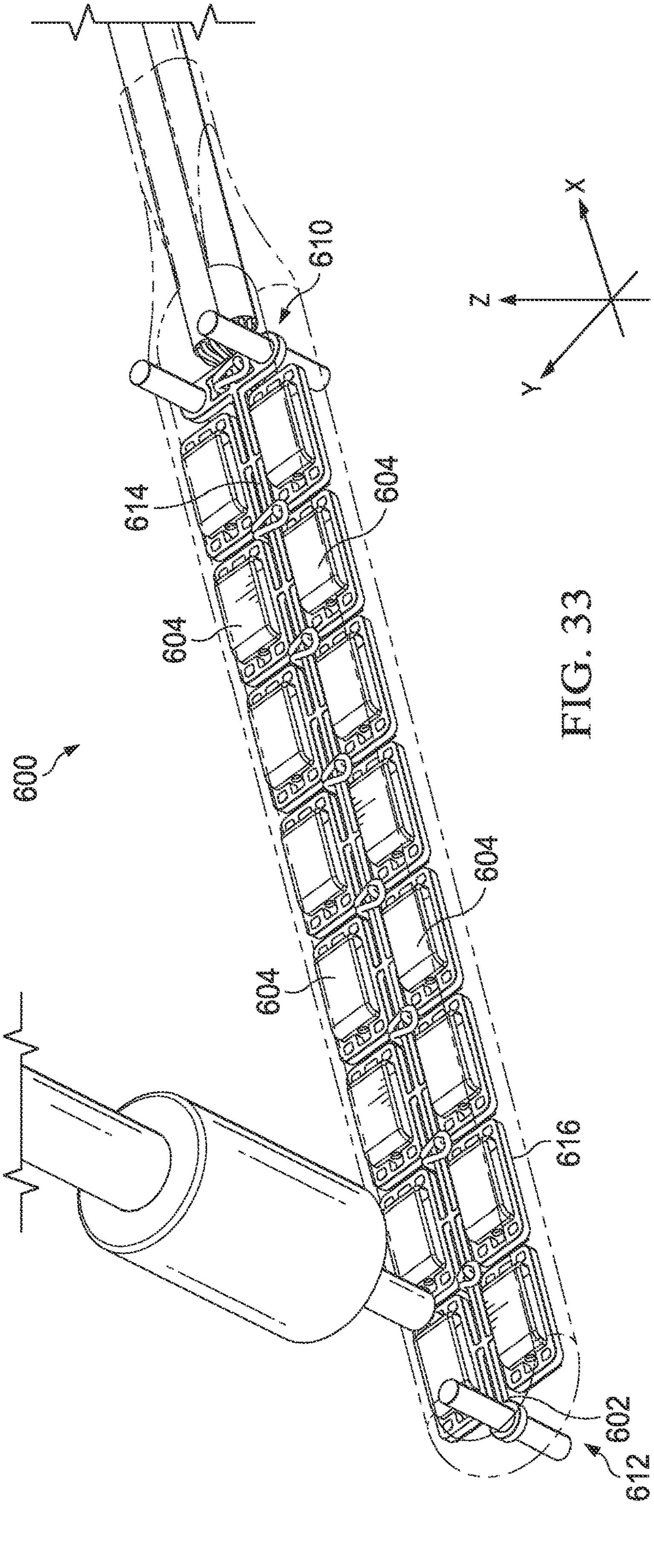
Figure 34:
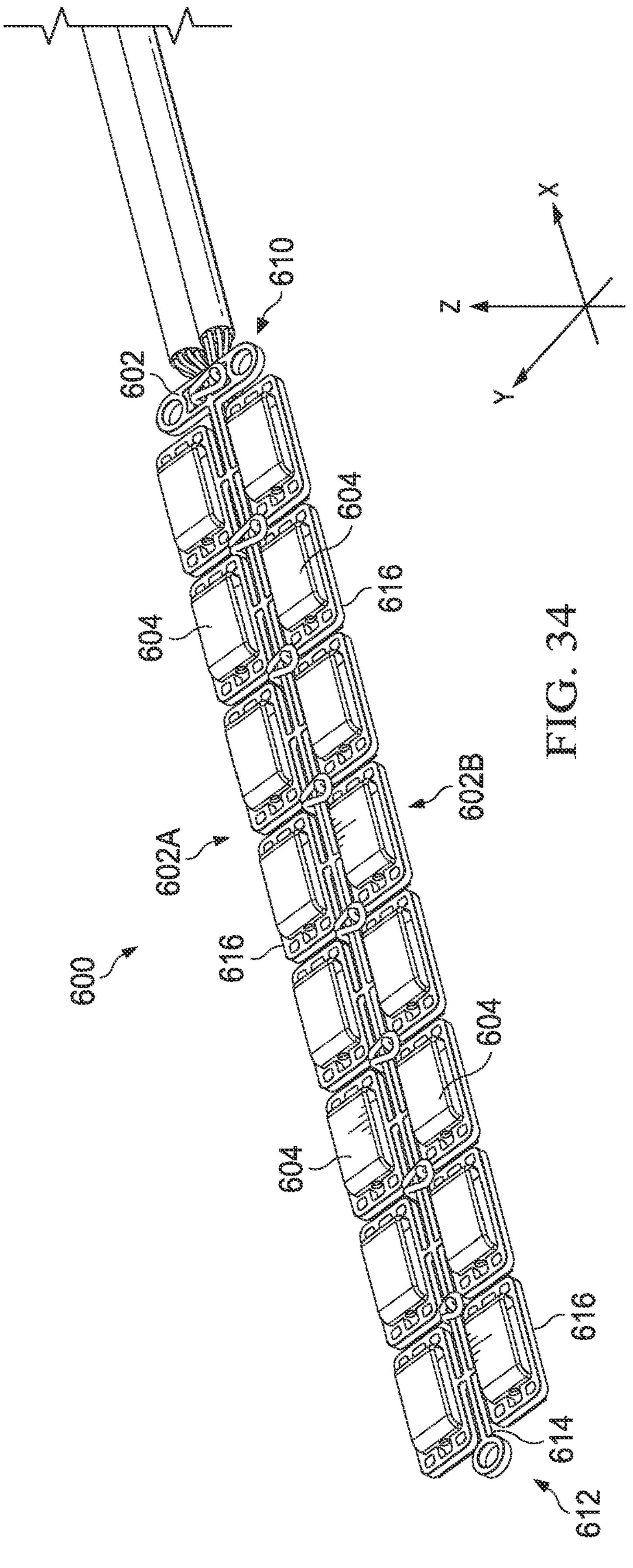

FIGS. 31-48 illustrate various views of yet another embodiment of an electrode assembly 600 according to various aspects of the present disclosure. In more detail, FIG. 31 illustrates a planar top view of the electrode assembly 600 with a molding material 601 applied, FIG. 32 illustrates a planar top view of the electrode assembly 600 without the molding material 601, FIG. 33 illustrates a three-dimensional prospective view of the electrode assembly 600 with the molding material applied, FIGS. 34-35 illustrate a three-dimensional prospective view of the electrode assembly 600 at different viewing angles without the molding material applied.

Figure 35:
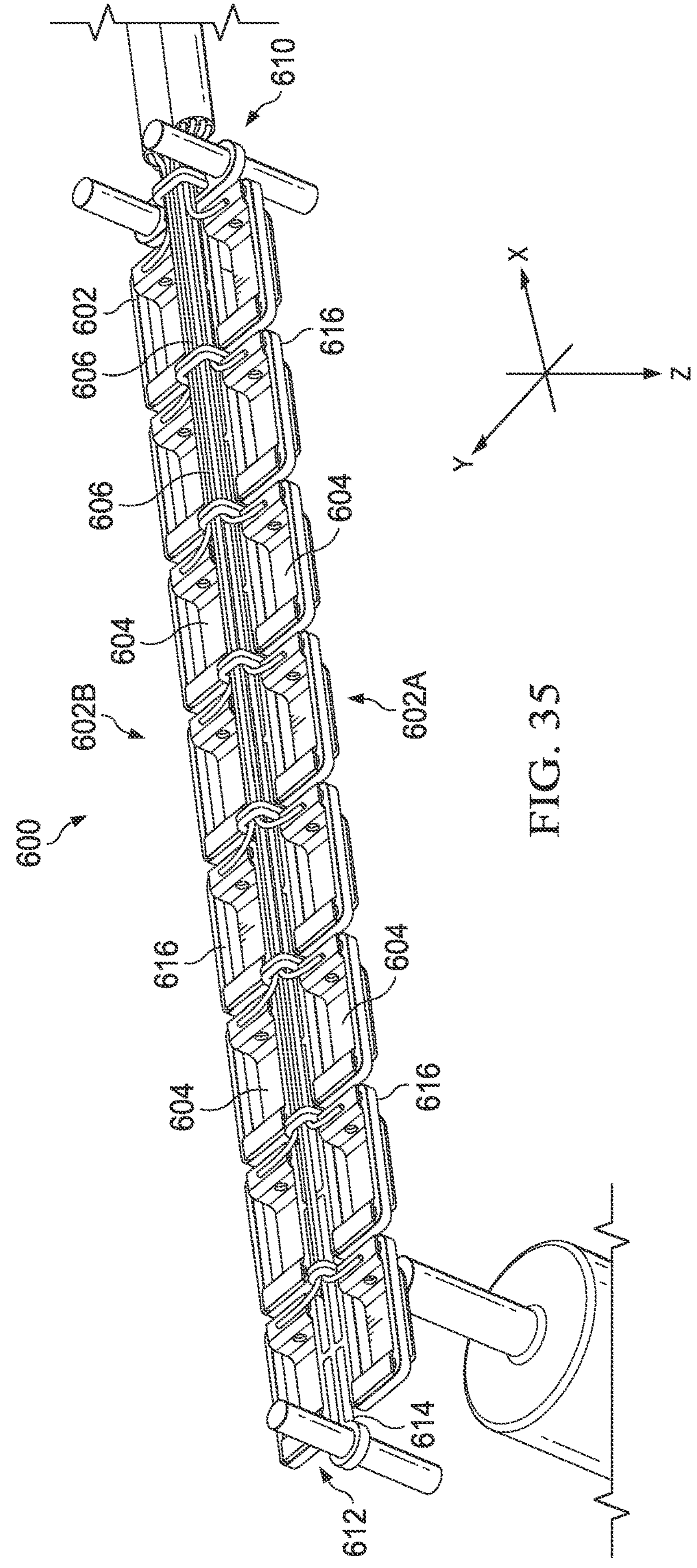

The electrode assembly 600 includes a substrate 602, a plurality of electrodes 604, and a wiring assembly 606 (shown clearly in FIG. 35). The substrate 602 extends from a proximal end 610 to a distal end 612 along the X-direction. Note that FIGS. 33-34 primarily illustrate the top side 602A (also referred to as a therapy side) of the electrode assembly 600, whereas FIG. 35 primarily illustrates the bottom side 602B (also referred to as a non-therapy side) of the electrode assembly 600.

The substrate 602 includes an elongate stem portion 614 and a plurality of individual electrode connection structures 616 that extend from the stem portion 614 to support the plurality of electrodes 604 therein. The stem portion 614 is centrally located between a plurality of adjacent pairs of the electrode connection structures 616 and supports the wiring assembly 606. The electrode connection structures 616 are arranged into a plurality of columns that each extend in the X-direction, as well as a plurality of rows that each extend in the Y-direction. Although the embodiment illustrated in FIGS. 31-35 illustrate two columns and eight rows of the electrode connection structures 616, other numbers of columns and rows may be implemented in alternative embodiments.

Figure 36:
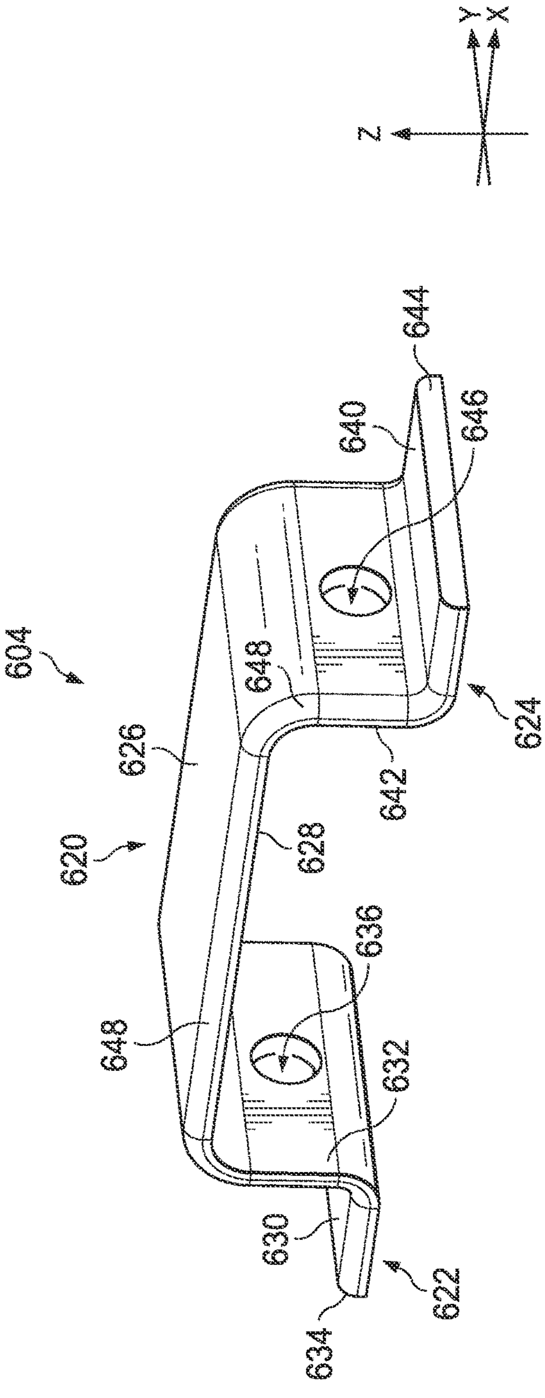
Figure 37:
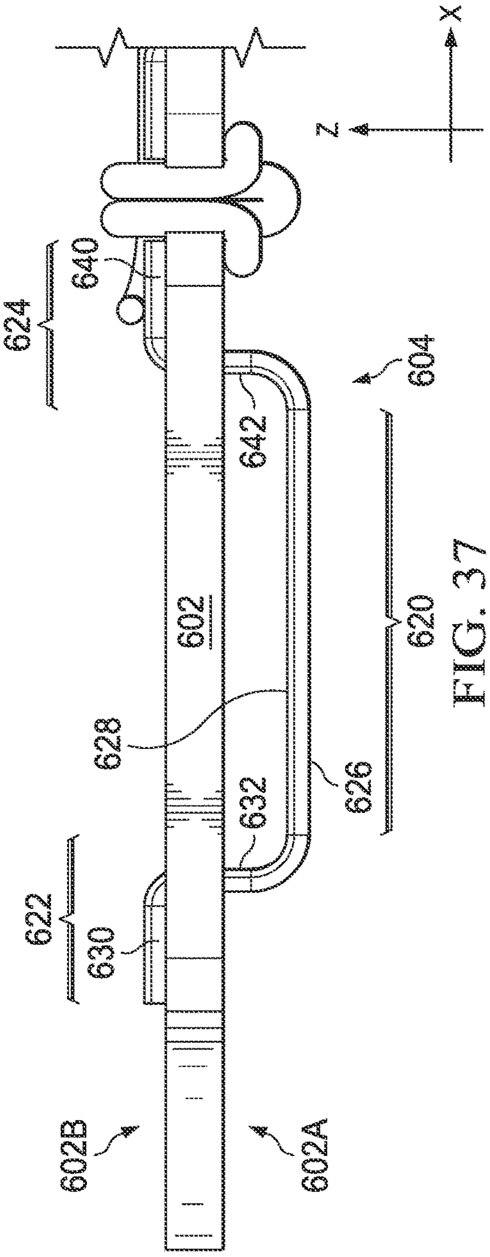
Figure 38:
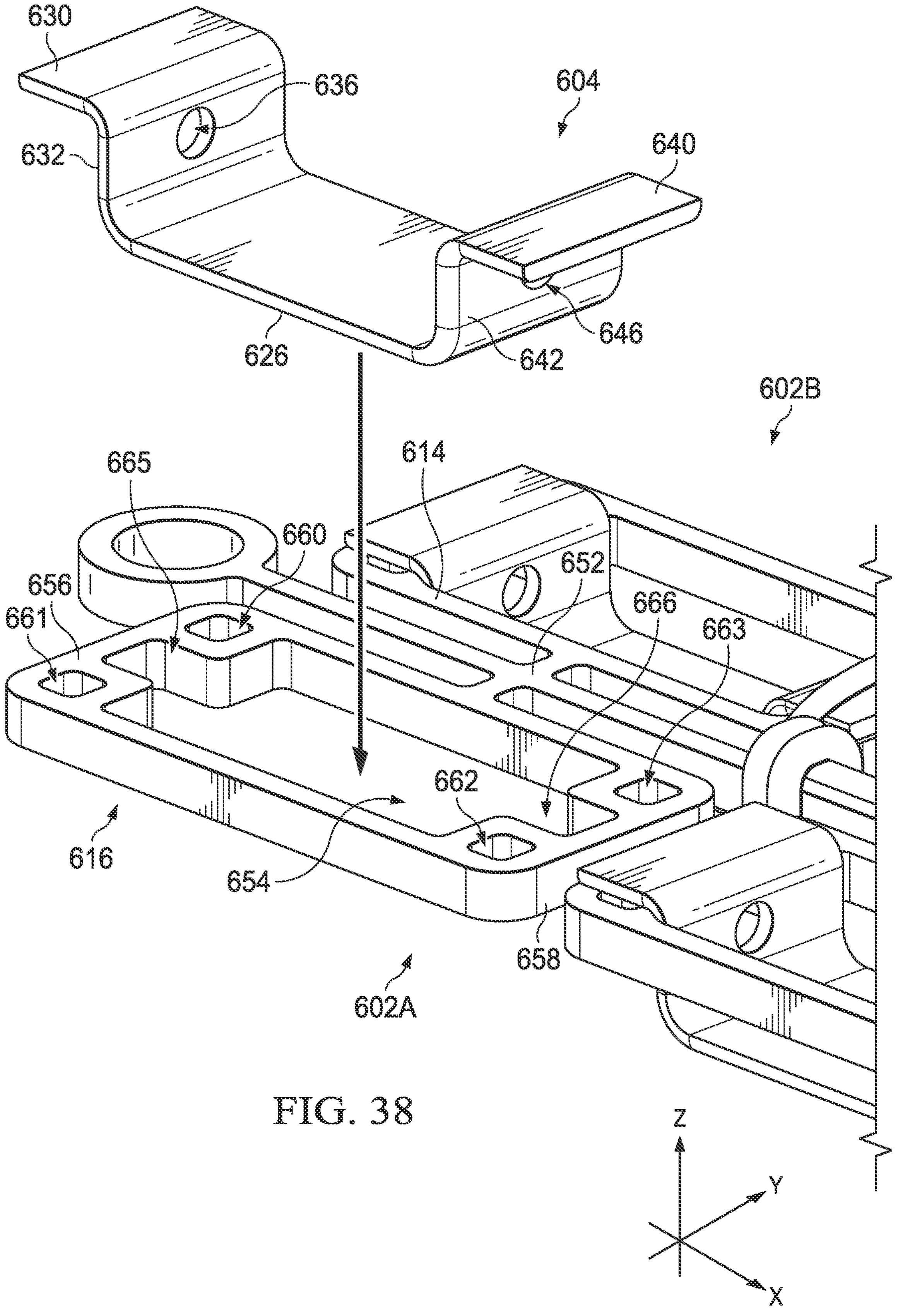

Each of the electrode connection structures 616 defines a respective opening (which will be discussed below in more detail with reference to FIG. 38) through which a respective electrode 604 is inserted and housed. FIG. 36 illustrates a three-dimensional perspective view of an electrode 604, and FIG. 37 illustrates a side view (in an X-Z plane) of the electrode 604 along with a portion of the substrate 602. As illustrated in FIGS. 36-37, the electrode 604 includes a central portion 620, a first leg portion 622 and a second leg portion 624 positioned on an opposite side (e.g., in the X-direction) of the central portion 620 from the first leg portion 622. The central portion 620 includes a stimulation surface 626 (also referred to as a therapy surface or an outside surface) positioned to face away from the substrate 602 in the Z-direction and contact the user to deliver stimulation thereto. The stimulation surface 626 is illustrated as generally planar and of a desired surface area to deliver enough stimulation to an area of a patient. Opposite the stimulation surface 626 is an inside surface 628 (also referred to as a non-therapy surface), where contact could be made with an associated wire in some embodiments. However, as will be discussed in more detail below with reference to FIGS. 40-41, the electrical contact between the electrode 604 and the associated wire is made not at the inside surface 626, but at the first leg portion 622 or the second leg portion 624, according to a resistance welding process.

In some embodiments, the electrode 604 is made using the strip electrode process discussed above with reference to FIGS. 26-30. For example, the electrode 604 may be made by unrolling a single strip or piece of metal material (see FIG. 27), cutting a portion of the metal (see FIG. 28) with a predefined length, where the cut-portion corresponds to a single electrode 604, bending the end segments of the cut-portion (see FIG. 29) so that they each protrude vertically in the Z-direction, and thereafter bending portions of the vertically protruding segments in the X-direction (see FIG. 30). Note that very little (to none) metal material is wasted in the strip electrode formation process herein. In contrast, conventional methods of fabricating electrodes may lead to excessive amounts of scrap metal waste, which is wasteful and undesirable.

Referring back to FIGS. 36-37, as a result of the strip electrode formation process, the electrode 604 has the first leg portion 622 and the second leg portion 624. The first leg portion 622 includes a horizontal portion 630 and a vertical portion 632 connecting the horizontal portion 630 with the central portion 620. The horizontal portion 630 terminates at an end portion 634, whereas the vertical portion 632 locates the stimulation surface 626 away from the substrate 602. An aperture 636 is positioned in the vertical portion 632. In a similar manner, the second leg portion 624 includes a horizontal portion 640 and a vertical portion 642. The horizontal portion 640 terminates at and end portion 644, whereas the vertical portion 642 locates the stimulation surface 626 away from the substrate 602. An aperture 646 is positioned in the vertical portion 642. After the electrode assembly 604 undergoes molding, the apertures 636 and 646 may hold silicone (or another suitable molding material) therein, which helps to further increase the mechanical adhesion between the electrode 604 and the substrate 602. The apertures 636 and 646 are circular in shape in the embodiment of FIG. 36, but they may be shaped differently in other embodiments, such as elliptically-shaped, square-shaped, rectangular-shaped, etc.

Another unique physical characteristic of the electrode 604 is that is has curved or rounded edges 648 (also referred to as roll formed edges). Depending on its location within the electrode 604, the curved edge 648 may curve in different directions. For example, at the central portion 620 and the horizontal portions 630 and 640, the curved edge 648 curves in the Y-direction and the Z-direction. At the vertical portion 632 or 642*m* the curved edge 648 curves in the X-direction and the Y-direction. As such, with the possible exception of the end portions 634 and 644, the electrode 604 does not have sharp edges (e.g., edges formed by 90-degree angles). In particular, the stimulation surface 626 (through which the electrical stimulation therapy is delivered to a patient) includes a substantially flat/planar surface that terminates in the curved edges 648. Such curved edges 648 help reduce or prevent potential cuts (or other potential damages) to the body tissue of the patient.

To produce the electrode assembly 600, each of the plurality of electrodes 604 is positioned in the substrate 602. As illustrated in FIG. 38, which is a perspective view of an example electrode 604 and example electrode connection structure 616, the electrode 604 is inserted into the corresponding electrode connection structure 616 from the bottom side 602B (i.e., non-therapy side) of the electrode assembly 600. Electrode connection structure 616 is connected with the elongate stem portion 614 through a bridge portion 652 and defines an opening 654 having a first coupling end 656 and a second coupling end 658 spaced apart from the first coupling end 656 (in the X-direction). The first coupling end 656 includes openings 660 and 661 that each extend in the Z-direction, and the second coupling end 656 includes openings 662 and 663 that each extend in the Z-direction. A gap 665 separates the openings 660 and 661 in the Y-direction, and a gap 666 separates the openings 660 and 661 in the Y-direction. The gaps 665 and 666 are connected to the opening 654 and may each be considered a part of the opening 654. Alternatively, the gaps 665 and 666 may also be considered parts of the first coupling end 656 and 658, respectively.

Although illustrated as generally rectangular with adjoined gaps 665 and 666, the opening 654 can have any shape as desired. The coupling ends 656 and 658 each establishes a connection point with the electrode 604 to facilitate a press or interference fit between the electrode 604 and the electrode connection structure 616. In particular, the coupling end 656 establishes a press or interference fit with the horizontal portion 630 of the electrode 604, and the coupling end 658 establishes a press or interference fit with the horizontal portion 640 of the electrode 604. For example, during assembly, the stimulation surface 626 of the electrode 604 is faced toward the opening 654 on the bottom side 602B and inserted through the opening 654 until the horizontal portions 630 and 640 make physical contact with the coupling ends 656 and 658, respectively. As a part of the press fitting or interference fitting process, much force may be exerted to the substrate 602 (including to the coupling ends 656 and 658). Advantageously, the implementation of the openings 660-663 herein allows the coupling ends 656 and 658 to better tolerate the force exerted thereto by deflecting or bending without breaking. Had the openings 660-663 not been implemented (which is the case for conventional electrode assemblies), the thin walls of the substrate 602 may rip or be torn off during the press fitting process or during other processes that could exert force on the substrate 602.

The electrode 604 and the electrode connection structure 616 are also sized to cooperate with one another to establish an interference fit upon insertion, such that the electrode 604 can be secured to the substrate 602. Thereafter, wiring is connected to the electrode 604, and an overmold is applied to the assembly 600. In the embodiment illustrated, a distance between vertical portions 632 and 642 is selected such that coupling ends 656 and 658 engage and hold the electrode 604 during further manufacturing processes such as wiring connection and overmolding.

Figure 39:
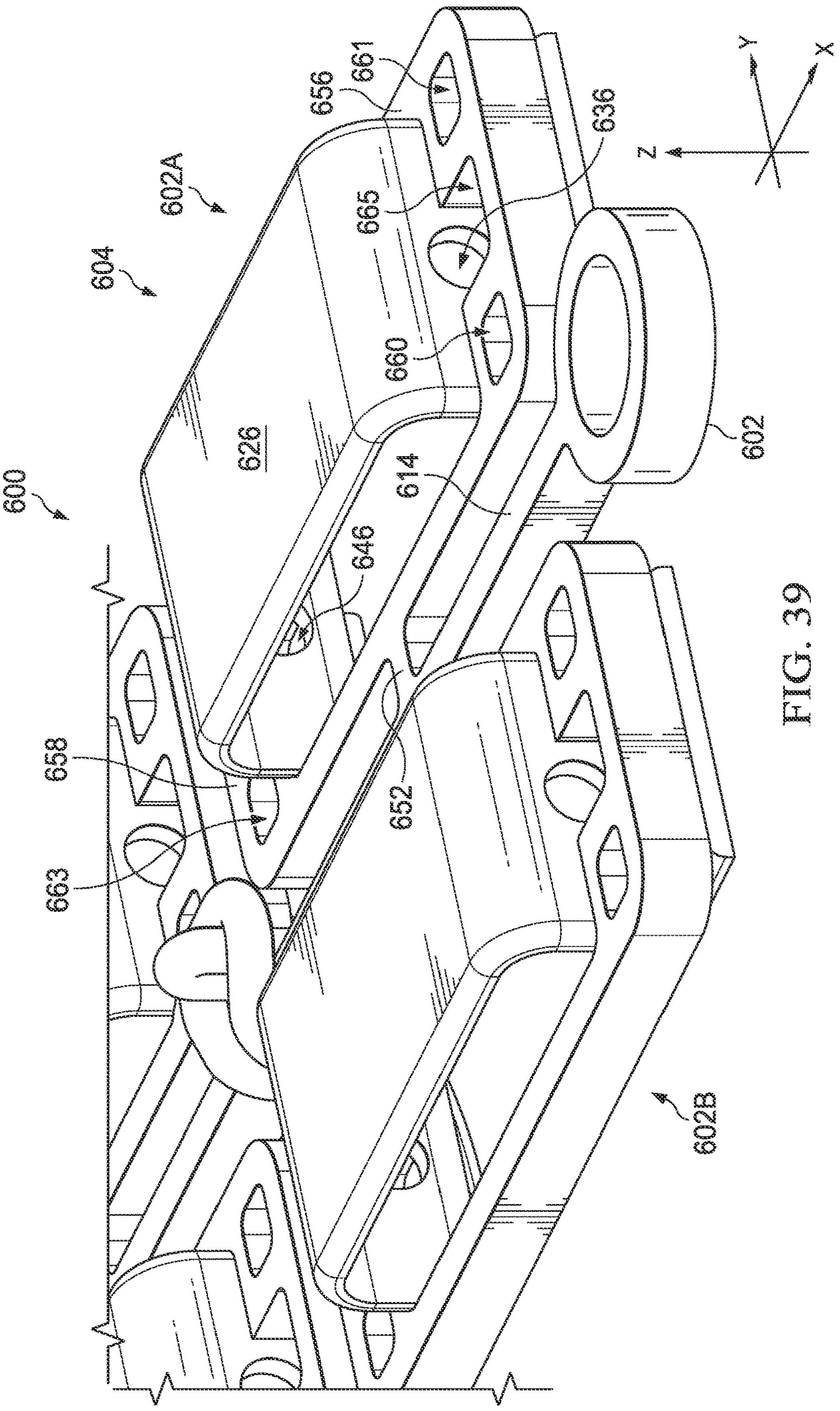

Referring now to FIG. 39, a magnified three-dimensional perspective view of a portion of the electrode assembly 600 is illustrated. After insertion of the electrodes 604, the apertures 636 and 646 are exposed to, and aligned with, the gaps 665 and 666, respectively. As a result, an overmolding material (e.g., silicone) can enter through the gaps 665 and 666 into the apertures 636 and 646, which assists in securing electrodes 604 in place after the overmolding material has cured. For example, the portions of the overmolding material that remain in the gaps 665-666 and in the apertures 636 and 646 after being cured will provide another mechanical mechanism to help attach each of the electrodes 604 to the substrate 602 (specifically, to their respective electrode connection structure 616). In this manner, the attachment of the electrodes 604 to the substrate 602 is not entirely dependent on the results of the press fitting between the leg portions of the electrode 604 with their respective coupling ends 656 and 658 of the electrode connection structure 616, since the adhesive forces provided by the overmolding material in the gaps 665-666 and the apertures 636 and 646 will also help to lock the electrodes 604 in place. As a result, the electrode assembly 600 of the present disclosure has enhanced structural integrity compared to conventional electrode assemblies, since the separation between the electrodes 604 and the substrate 602 is less likely to occur.

One of the unique physical characteristics distinguishing the embodiment of the electrode assembly 600 from the conventional electrode assemblies is that no portion of the substrate 602 is located underneath (on the bottom side 602B) the inside surfaces 628 of the electrodes 604. Such a design improves the performance and reliability of the electrode assembly 600. In more detail, conventional substrates (where portions thereof are typically disposed below the electrodes) may be very thin. The thinness of the substrate may lead to difficulties in performing certain mechanical processes such as press fitting to fit the electrodes on such a thin substrate, since these mechanical processes may inadvertently deform or even break the relatively thin substrate. As such, it may be desirable to thicken the substrate (e.g., in the Z-direction vertically) to prevent the substrate from being damaged by the mechanical processes such as press fitting. Unfortunately, thickening the substrate may render the substrate too rigid or stiff, which means that the substrate may not be sufficiently pliable when the electrode assembly is implanted inside a patient's body. This could cause patient discomfort and/or lead to degradations in the efficacy of the stimulation therapy delivered by the electrodes. In addition, the molding material (e.g., silicone) of the electrode assembly may move around due to the deformation of the substrate. If the molding material within the electrode pushes against the electrode with a sufficient amount of pressure in an outwardly direction, it could cause the electrode to detach from the substrate, which may not only render the electrode assembly ineffective in delivering the intended stimulation therapy, but could also pose a serious health risk to the patient.

To solve these problems associated with conventional electrode assemblies discussed above, FIGS. 31-39 of the present disclosure implements an embodiment where much of the surface area of the substrate 602 has been eliminated, which allows the substrate 602 to be thicker than otherwise suitable. In other words, by eliminating the portions of the substrate 602 underneath the inside surfaces 628 of the electrodes 604, the remaining portion of the substrate 602 is much smaller than conventional substrates (e.g., in terms of total mass or volume). This reduction in surface area of the substrate 602 allows the substrate 602 to be made thicker, such that it can tolerate the mechanical processes such as press fitting without being deformed. Meanwhile, due to the reduction of a substantial amount of surface area, the thickened substrate 602 still maintains sufficient pliability and/or flexibility to not cause discomfort inside a patient's body. Furthermore, since no portion of the substrate 602 is disposed below the electrodes 604, the molding material below the electrodes 604 will not be pushed against the electrode 604 by the (non-existent) substrate. Consequently, the molding material is unlikely to cause detachment of the electrodes 604 from the substrate 602, even if the substrate 602 undergoes deformation or otherwise bends.

Figure 40:
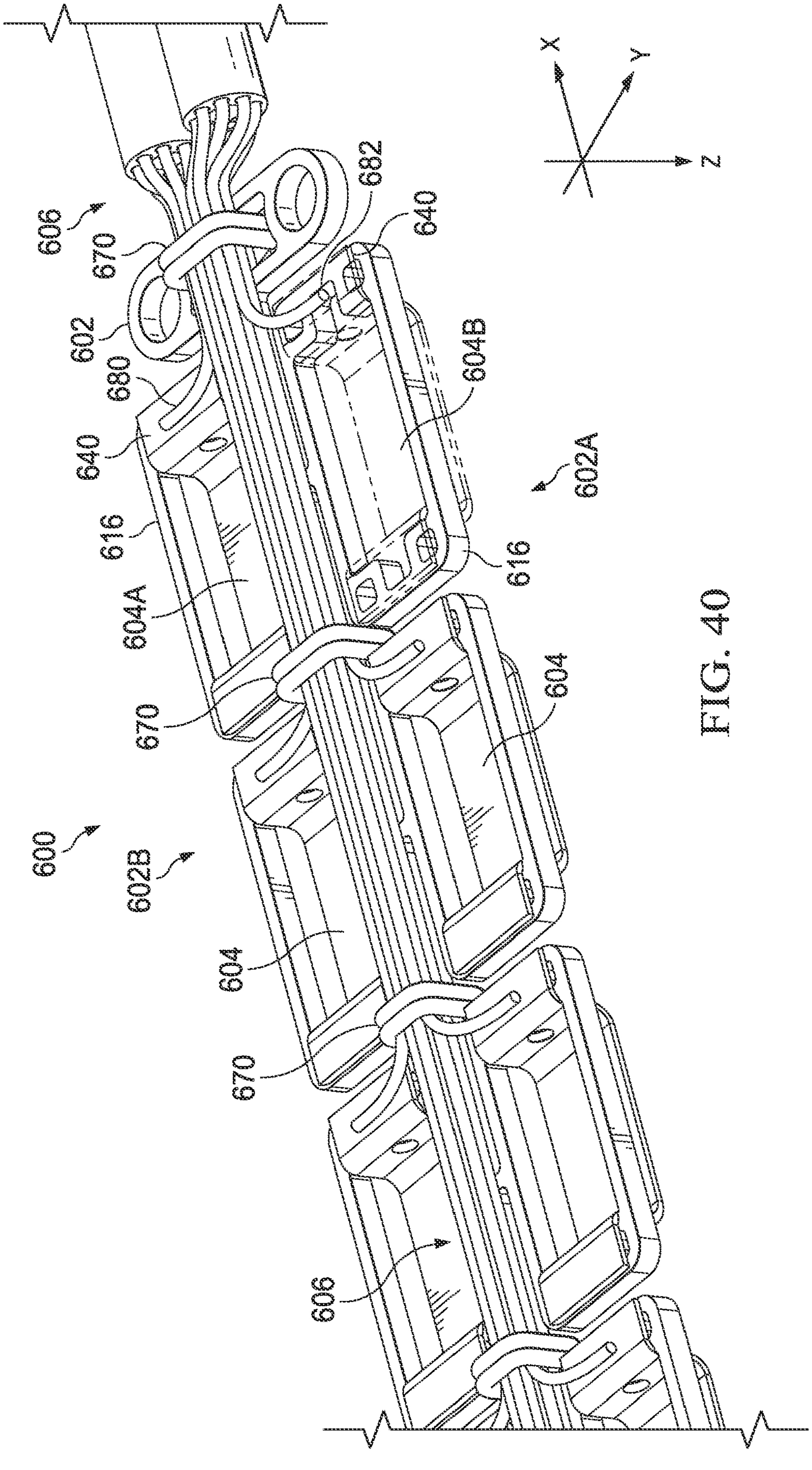

FIG. 40 is a magnified three-dimensional perspective view of a portion of the electrode assembly 600 shown in FIG. 35. Referring to FIGS. 40 and 35, a wiring assembly 606 is used to electrically connect a stimulation source to each electrode 604. The wiring assembly 606 includes a plurality of individual wires from one or more leads. In particular, the wiring assembly 606 includes one respective wire for each electrode 604 in the electrode assembly 600, where the wires are arranged into a wiring bundle. In the embodiment shown in FIGS. 35 and 40, the wiring assembly 606 is positioned on the bottom side 602B (i.e., the non-therapy side) of the electrode assembly 600. Each individual wire may be insulated along its length to prevent electrical shorting with adjacent wires.

The wiring assembly 606 also includes one or more banding mechanisms 670 spaced apart along the stem portion 614. The banding mechanisms 670 are used to secure the wires to the substrate 602. In the illustrated embodiment, the banding mechanisms 670 may be implemented in the form of a girth hitch to secure itself and the wires to the substrate 602, although other knots and other forms of securing the wiring assembly 606 to the substrate 602 can be used. For example, the banding mechanisms 670 can be sutures. Other mechanisms can further be employed.

Individual wires of the wiring assembly 606 can be connected to each of the electrodes 604. For example, as shown in FIG. 40, an individual wire 680 branches off or "fans out" from the wiring bundle of the wiring assembly 606 and is welded to the horizontal portion 640 (i.e., one of its legs) of the electrode 604A from the non-therapy side 602A to establish electrical connection between the wire 680 and the electrode 604A. Similarly, an individual wire 682 branches off from the wiring bundle of the wiring assembly 606 and is welded to the horizontal portion 640 of the electrode 604B from the non-therapy side 602B to establish electrical connection between the wire 682 and the electrode 604B. Note that the electrode 604B is illustrated transparently to facilitate the reader's understanding of the present disclosure (e.g., to illustrate the various openings and gaps of the electrode connection structure 616 discussed above with reference to FIG. 39), though it is understood that the electrode 604B is opaque in actual implementation, as is the case for the rest of the electrodes 604. In any case, each of the wires of the wiring assembly 606 branches off from the wiring bundle after passing by a given banding mechanism 670, so that it can be attached to the horizontal portion 640 of the respective electrode.

Figure 41:
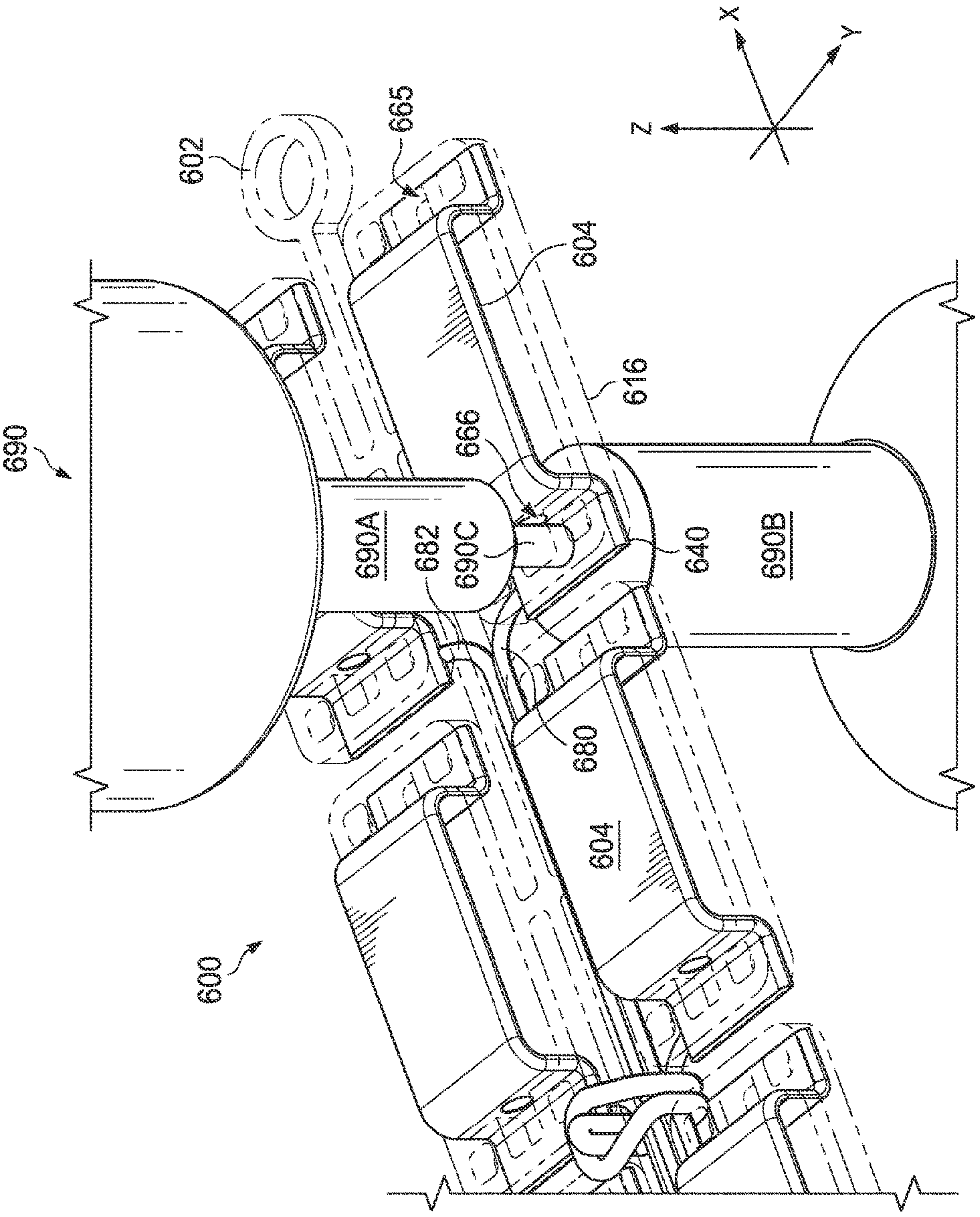

FIG. 41 illustrates a three-dimensional perspective view of a portion of the electrode assembly undergoing a resistance welding process, in which the wires of the wiring assembly 606 are welded to the electrodes 604. For example, after a wire (e.g., the wire 680 or 682) is placed onto the non-therapy side surface of horizontal portion 640 of the electrode 604, a resistance welding tool 690 is used to weld the wires. The welding tool 690 may include a top component 690A and a bottom component 690B that are positioned on opposite sides of the substrate 602 and on opposite sides of the horizontal portion 640 of the electrode 604. The top portion 690A further includes a tip portion 690C that extends out in the Z-direction. The dimensions of the tip portion 690C and the gap 666 of the electrode connection structure 616 are configured such that the tip portion 690C will fit within the gap 666. This is made possible by the unique design of the electrode connection structure 616, i.e., the fact that it is configured to include such gaps 665 and 666.

As the bottom surface of the tip portion 690C of the welding tool 690 comes into physical contact with the top surface of the horizontal portion 640 of the electrode 604, and the top surface of the bottom portion 690B of the welding tool 690 comes into physical contact with the wire 680, both mechanical and electrical forces are applied to the welding tool 690 to achieve the welding between the electrode 604 and the wire 680. Specifically, a mechanical force may be applied to the top portion 690A to push it (including the tip portion 690C) downwards in the Z-direction, and/or another mechanical force may be applied to the bottom portion 690B to push it upwards in the Z-direction. Due to the application of these mechanical forces, the physical contact between the electrode 604 and the wire 680 is enhanced. Meanwhile, a high amount of electrical current may be applied to the top portion 690A and the bottom portion 690B of the welding tool 690. As the electrical current runs through the interface of the electrode 604 and the wire 680, the wire 680 becomes fused or welded to the horizontal portion 640 of the electrode 604. The process may repeat for each of the other electrodes 604 and their corresponding wires.

Note that since the horizontal portions 640 or 630 serve as flanges for catching the substrate 602, they may be interchangeably referred to as flanges of the electrode 604. Therefore, the wire-to-electrode welding process described herein may also be referred to as a flange welding process. In addition to achieving good mechanical and electrical connections between the wires (such as the wires 680 and 682) and their corresponding electrodes 604, the welding process herein also simplifies certain other fabrication processes. For example, conventional processes of attaching the wires to the electrodes first have to use a first laser to ablate the wires (e.g., cutting the excess portions off), and then use a second and different laser to weld the wires to their corresponding electrodes. In comparison, the fusing of the wires and the electrodes according to the resistance welding process herein leads to a weak spot at where each wire is sticking out of the substrate 602 in the Y-directions. The fabrication process may take advantage of such weak spots by simply snapping off the wires at these weak spots. In other words, due to the resistance welding process performed herein to weld the wires and the electrodes 604 together, the present disclosure need not rely on lasers to weld or cut off the wires, which would have been complicated and costly.

Figure 42:
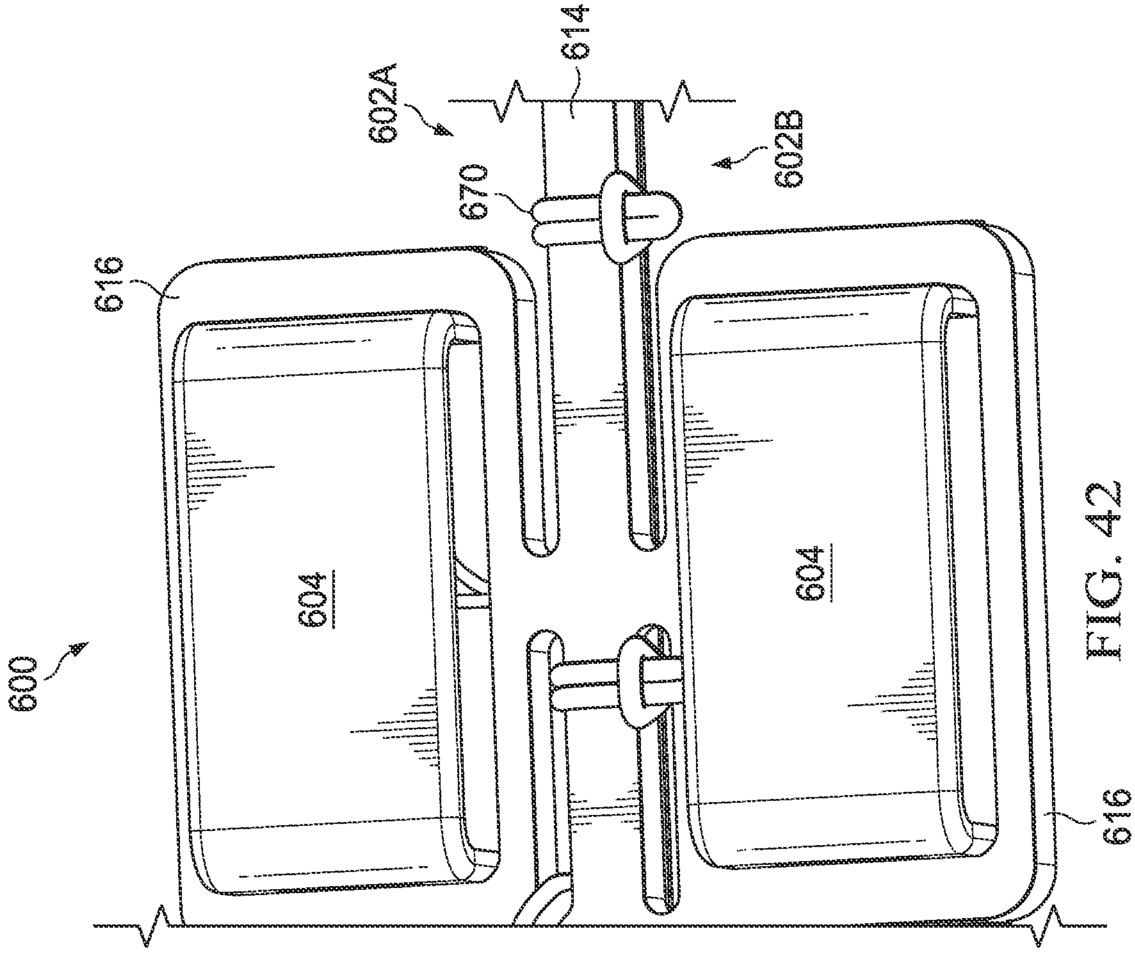

Another problem plaguing conventional electrode assembly design is wire management. Since the wires (such as the wires 680 or 682) are so small, as are the electrodes 604, improper wire management could increase fabrication difficulties or cause the failure of the electrode assembly. To overcome these problems, the present disclosure utilizes various banding techniques to manage the wires. For example, referring to FIG. 42, which is a three-dimensional perspective view of a portion of the electrode assembly 600, a banding mechanism 670 in the form of a girth hitch is illustrated. The banding mechanism 670 may have a silicone material composition and may circumferentially wrap around the elongate stem portion 614 of the substrate 602, thereby securing the wiring assembly 606 that is located on the bottom side 602B of the electrode assembly 600. Note that since the wiring assembly 606 is not directly visible in FIG. 42, since the elongate stem portion 614 obstructs the view of the wiring assembly 606. It is also understood that FIG. 42 illustrates the banding mechanism 670 from the therapy side 602A, while the non-therapy side 602B of the banding mechanism 670 is illustrated in FIG. 40.

Figure 43:
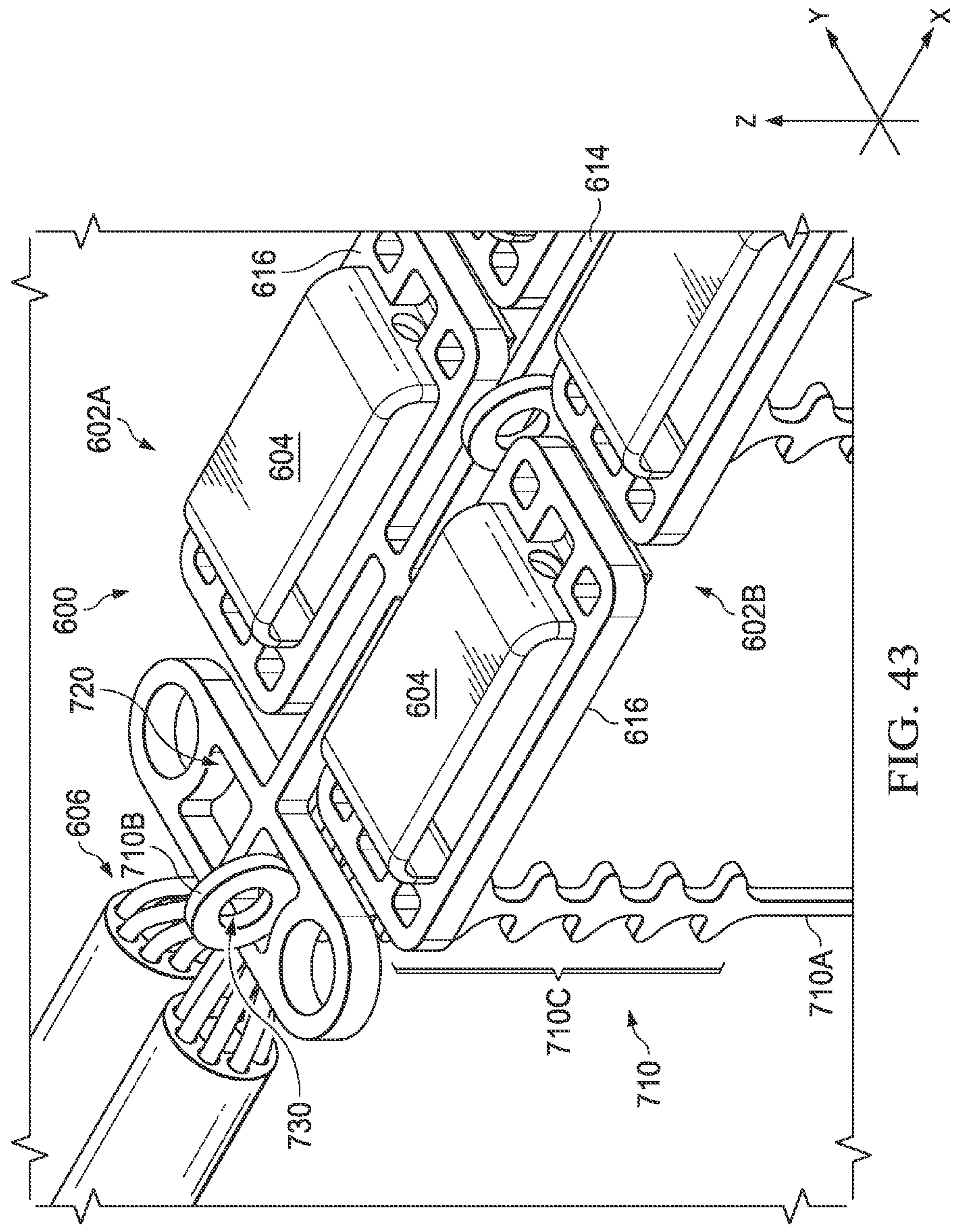

FIGS. 43-46 illustrate a series of three-dimensional perspective views of a portion of the electrode assembly to demonstrate the implementation of an alternative embodiment of a banding mechanism 710. Referring to FIG. 43, the banding mechanism 710 may have a silicone material composition and may be in the form of a zip tie. The banding mechanism 710 has a distal end portion 710A, a proximal end portion 710B, and a body portion 710C that joins the distal end portion 710A with the proximal end portion 710B. The body portion 710C includes a plurality of outwardly protruding ridges. Each of these ridges is angularly shaped, such that it is wider closer to the proximal end portion 710B and narrower closer to the distal end portion 710A. As shown in FIG. 43, the distal end 710A of the banding mechanism 710 is inserted through an opening 720 of the substrate 602. The proximal end portion 710B is wider than the opening 720 and therefore cannot be pushed through the opening 720. Note that the proximal end portion 710B itself defines an opening 730.

Figure 44:
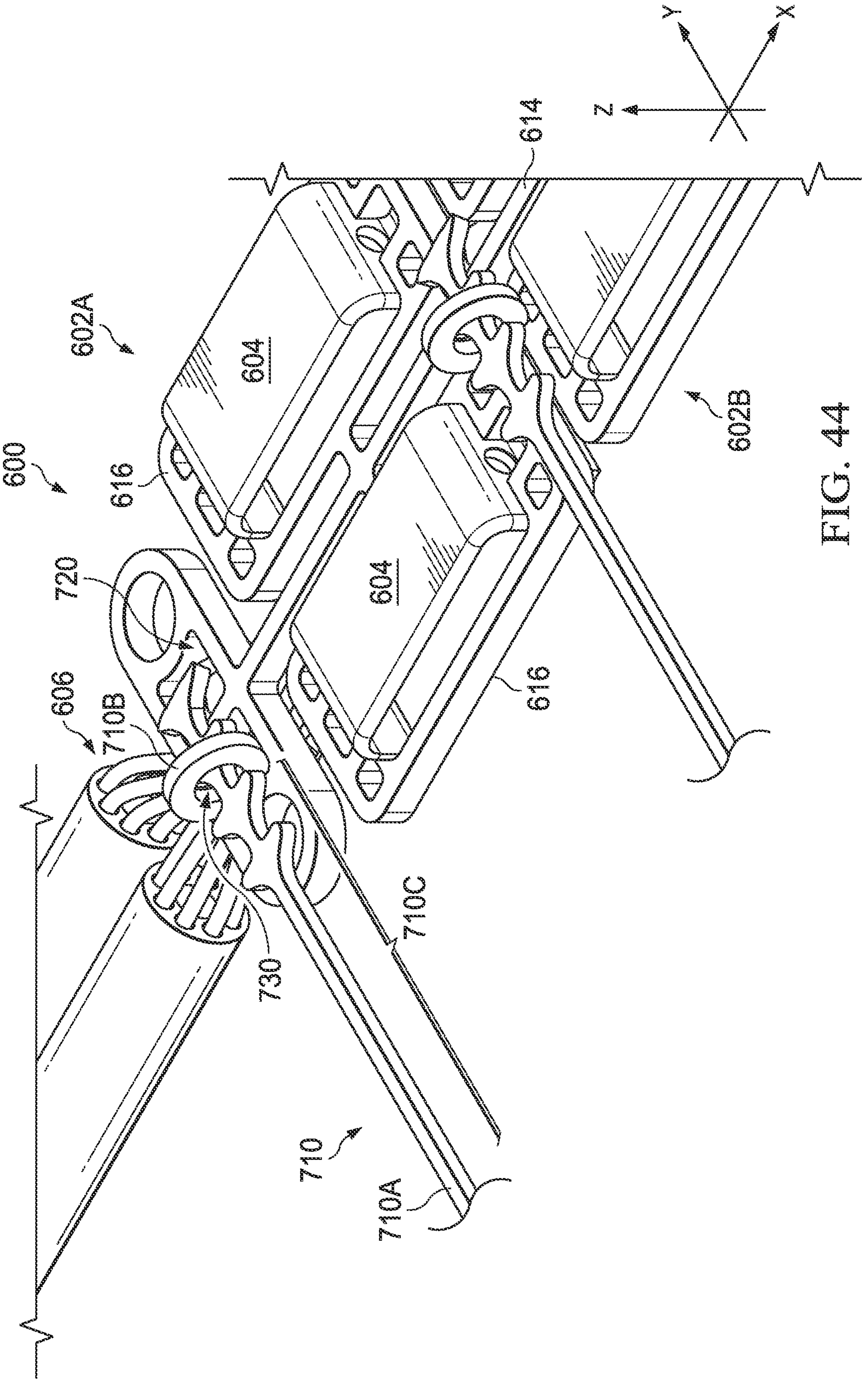

Referring now to FIG. 44, the distal end portion 710A of the banding mechanism 710 is folded around the wiring assembly 606 on the bottom side 602B and then threaded through the opening 730 on the top side 602A. The angular shape of the ridges of the banding mechanism 710 facilitates the insertion of the body portion 710C through the opening 730 in the −Y direction, but prevents the backward movement of the body portion 710C through the opening 730 in the +Y direction. In other words, the insertion of the body portion 710C through the opening 730 is uni-directional. The insertion of the body portion 710C through the opening 730 effectively ties a knot around the wiring assembly 606 and the elongate stem portion 614 of the substrate. At this point, the distal end portion 710A and a substantial amount of the body portion 710C of the banding mechanism 710 extend laterally beyond the substrate 602.

Figure 45:
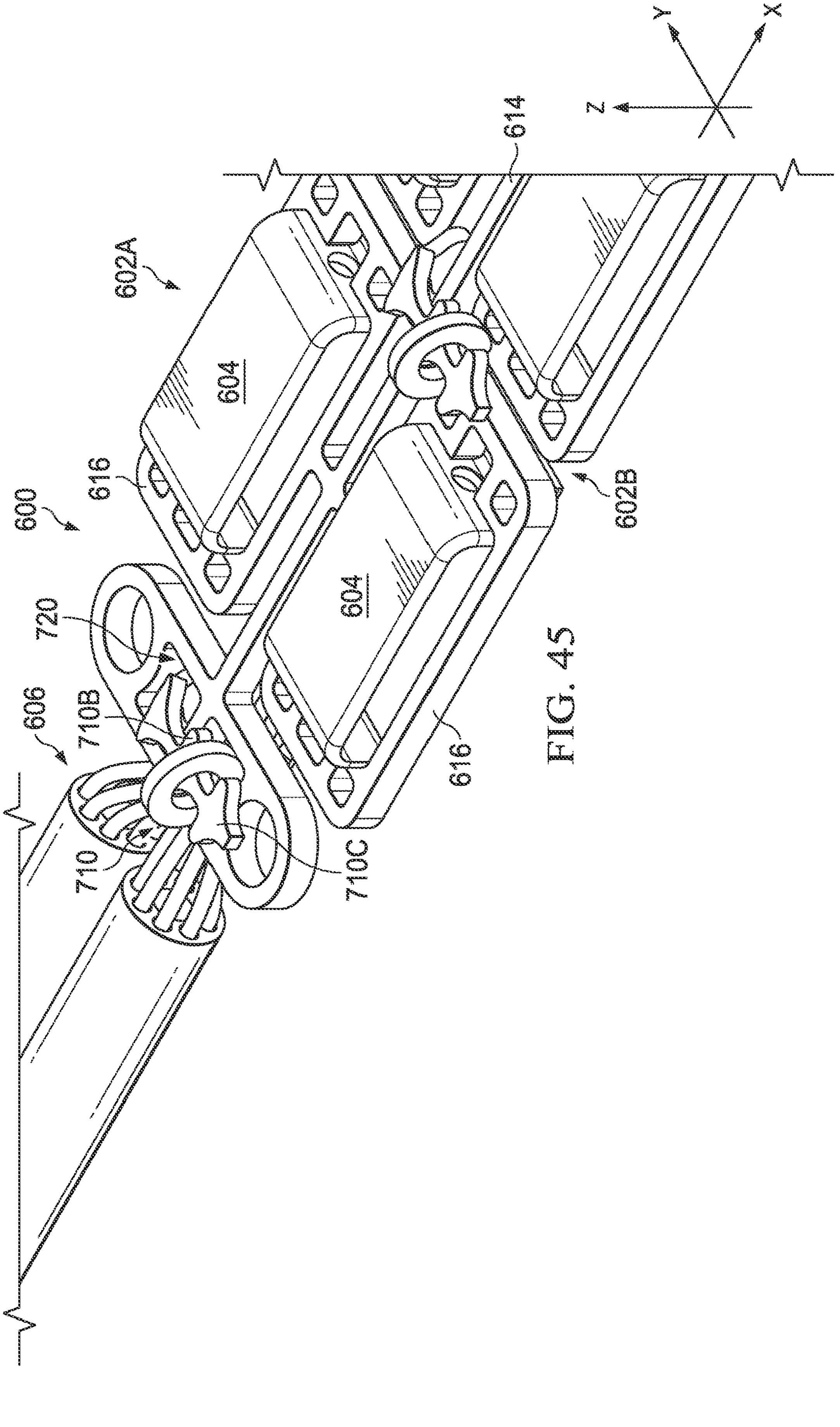

Referring now to FIG. 45, a substantial majority of the body portion 710C is removed for each banding mechanism 710, such that only one or two of the ridges may remain for each banding mechanism. The substantial removal of the body portion 710C makes the banding mechanism 710 more compact and makes it easier for the application of the molding materials on the electrode assembly 600 later.

Figure 46:
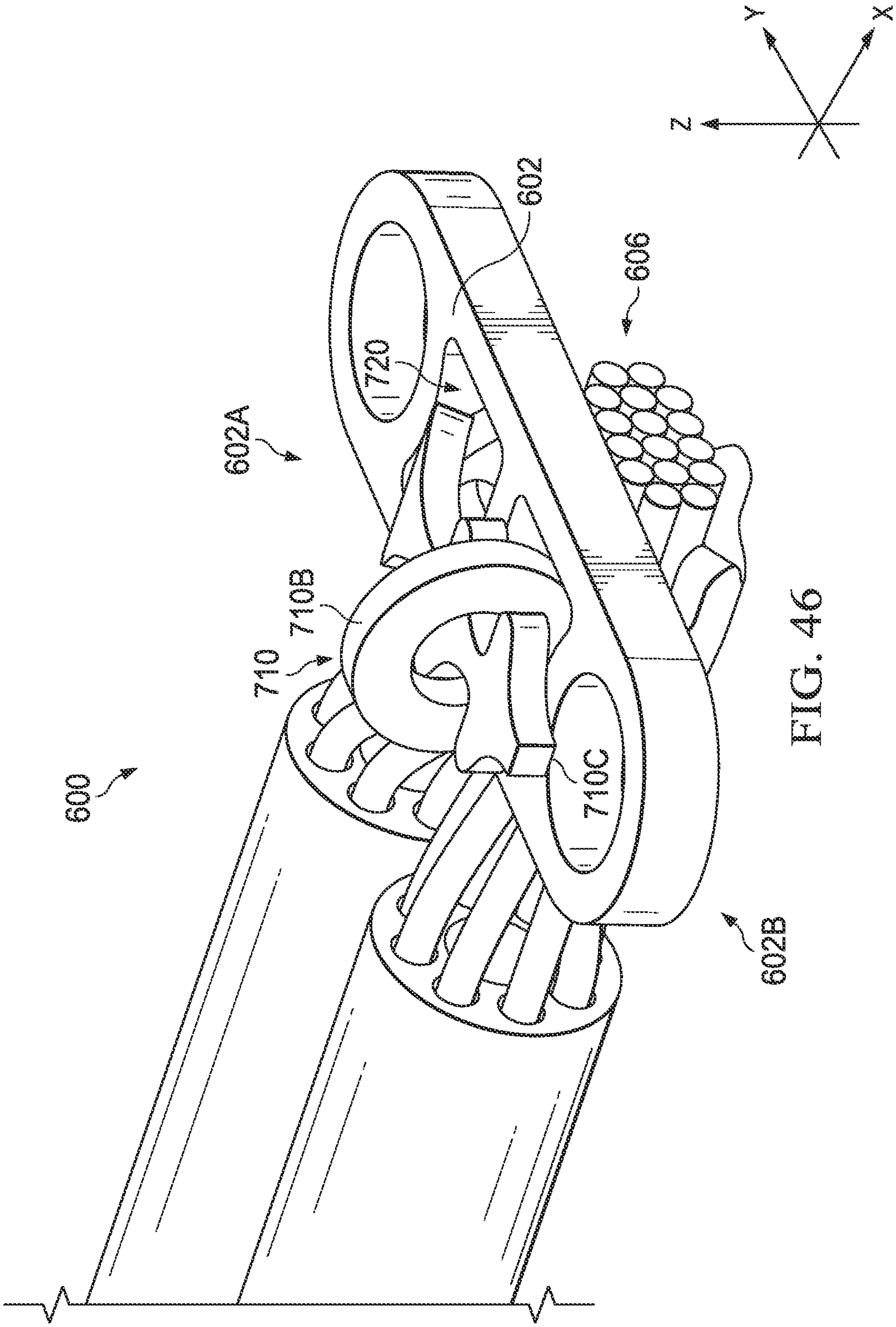

FIG. 46 further illustrates the banding mechanism 710 after the substantial removal of the body portion 710C. As FIG. 46 is a fragmentary perspective view, it clearly illustrates the bundle of wires of the wiring assembly 606 being tied to the substrate 602 by the banding mechanism 710.

Conventional electrode assemblies typically need to glue or otherwise attach the individual wires of a wiring assembly to trenches or troughs designed to hold the wires within. Unfortunately, if a wire is glued to a wrong trench or trough, the detachment of such a wire may be extremely difficult. In contrast, the present disclosure utilizes the banding mechanism 670 (e.g., a silicone girth hitch) or the banding mechanism 710 (e.g., a silicone zip tie) to hold the wiring bundle in place, so that the individual wires may be placed on their respective flanges of the electrodes 604. Up until the resistance welding process is performed to permanently attach the wires to the electrodes 604, it is easy to move or otherwise rearrange the individual wires. In this manner, correcting an inadvertently wiring mistake is substantially easier according to the embodiments of the present disclosure. In addition, as discussed above, it is simple to remove the excess portions of the wires after welding, as the welding creates weak spots in the wires, meaning that the excess portions of the wires can be snapped off easily. Therefore, the electrode assembly 600 of the present disclosure substantially simplifies the fabrication process, enhances device performance, and improves yield.

Figure 47:
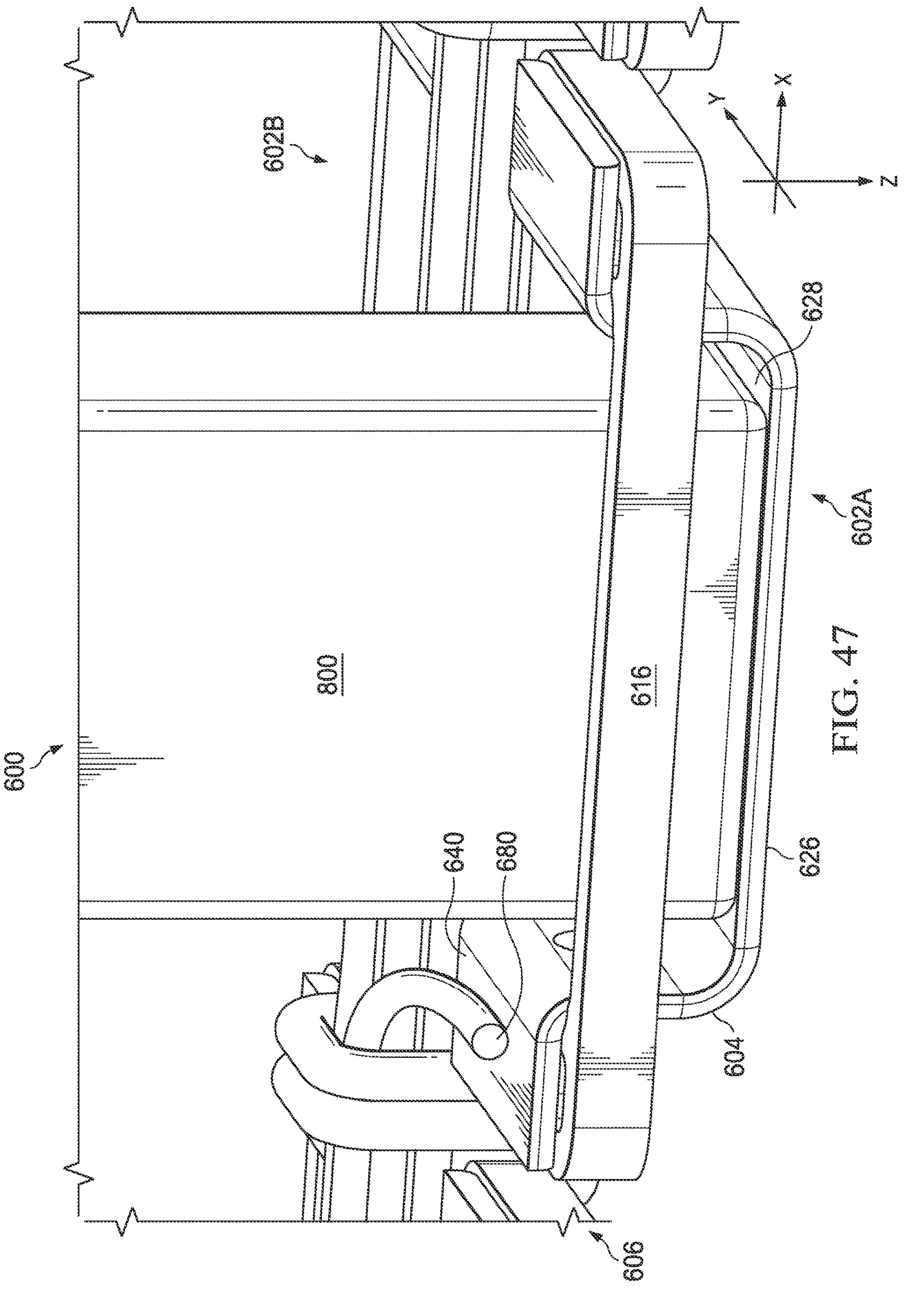

FIG. 47 illustrates a three-dimensional perspective view of a portion of the electrode assembly 600 undergoing an overmolding process according to embodiments of the present disclosure. In more detail, the overmolding process is performed after electrical connection between the wiring assembly 606 and each of the plurality of electrodes 604 is made via the resistance welding process discussed above. The overmolding process applies a molding material (e.g., silicone) to surround the electrode assembly 600. The molding material further secures the electrodes 604 to respective ones of the plurality of electrode connection structures 616. The molding material also offers some degree of structural rigidity to the electrode assembly and may serve as a protective material for the components embedded therein.

As a part of the overmolding process, a molding pin 800 is used to push against the inside surface 628 of the electrode 604 from the non-therapy side 602B. As clearly shown in FIG. 47, the sizes and dimensions of the molding pin 800 are configured such that it substantially occupies an entirety of the inside surface 628 of the electrode 604. In some embodiments, about 80%-100% of the inside surface 628 of the electrode 604 comes into direct physical contact with the molding pin 800. This is made possible by the fact that the wire 680 is welded onto the flange (i.e., the horizontal portion 640) of the electrode 604, rather than to the inside surface 628.

One advantage offered by the use of the molding pin 800 is the reduction or elimination of molding flash. In more detail, during the overmolding process, the molding pin 800 may be pressing the electrode 604 against another component of the molding tool (not illustrated herein) that is located on the therapy side 602A. In other words, while the molding pin 800 presses against the inside surface 628 of the electrode 604, the other component of the molding tool may be pressing against the stimulation surface 626 of the electrode 604. In conventional electrode assembly fabrication processes, the molding pin similar to the molding pin 800 would have been implemented as a much smaller pin, such that it only occupies a small portion of the inside surface of the electrode, since the wire would have also been welded onto the inside surface of the electrode. The small contact surface area between the molding pin and the electrode would have led to an imperfect fit between the molding components. For example, it could temporarily deform the electrode 604 during the molding process, which could cause the molding material to leak onto the stimulation surface 626 of the electrode 604. The molding material disposed on the stimulation surface 626 is known as molding flash, which is undesirable and needs to be removed, since it would otherwise block electrical stimulation signals from the electrode 604. Unfortunately, the removal of the molding flash may be difficult and time consuming.

In contrast, the molding process herein is performed using the much bigger molding pin 800 (again, made possible by welding the wires onto the flanges 640 of the electrode 604). Since the molding pin 800 herein can push against a substantial entirety of the inside surface 628 of the electrode 604, while the other molding component is pushing against a substantial entirety of the stimulation surface 626 of the electrode, the deformation of the electrode 604 is unlikely to occur. In other words, the now-much-bigger molding pin 800 can create a substantially tighter fit between the molding components, and this does not give much (if any) room for the molding material to leak onto the stimulation surface 626 of the electrode 604. In this manner, molding flash is substantially reduced or even completely eliminated according to the present disclosure.

Figure 48:
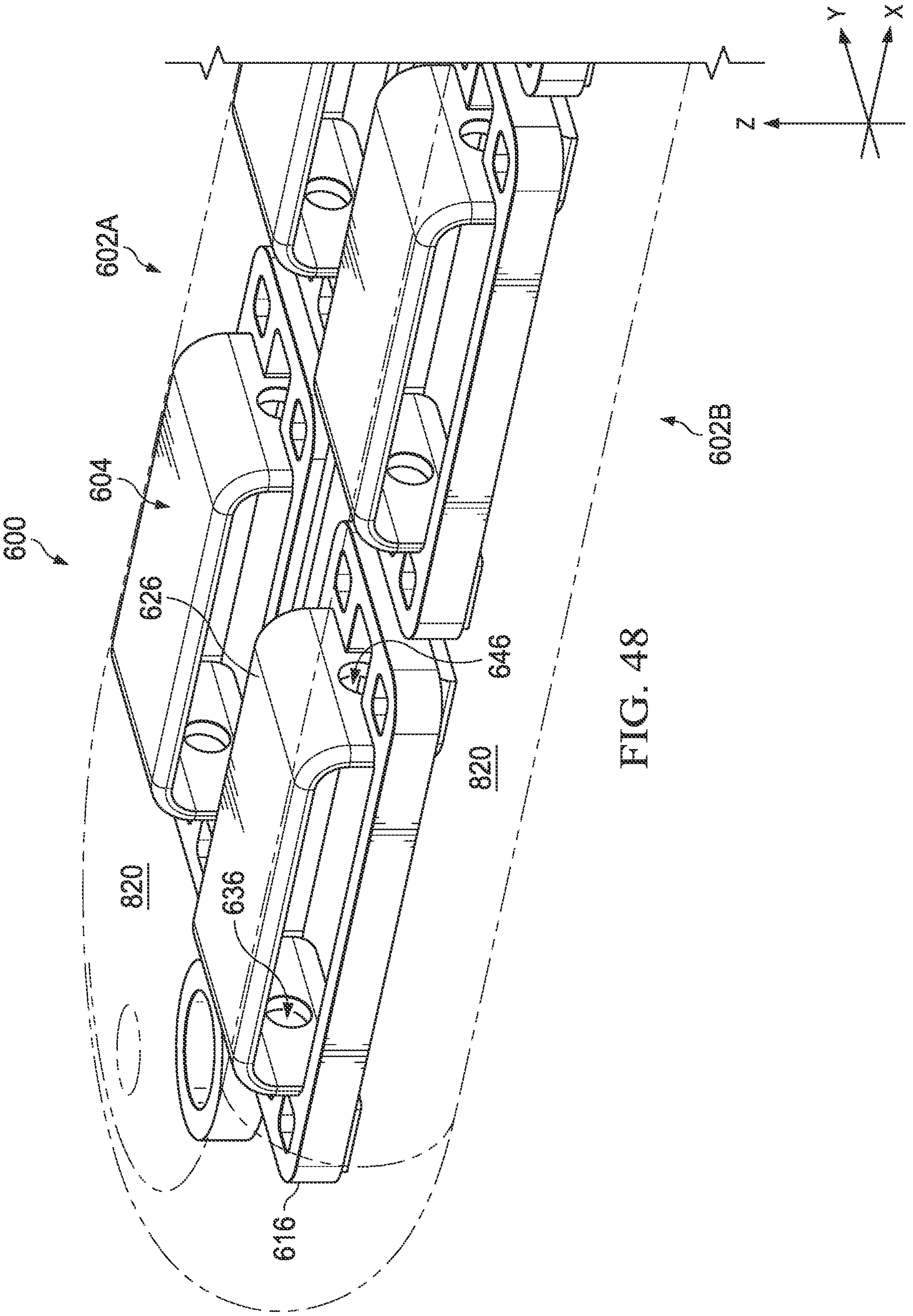

FIG. 48 illustrates a three-dimensional perspective view of a portion of the electrode assembly 600 after the overmolding process has been applied. The overmolding process applies a molding material 820 (e.g., silicone) around the electrode assembly 600, such that the electrodes 604 and their respective electrode connection structures 616 are embedded within the molding material 820. As discussed above, portions of the molding material 820 are located within the apertures 636 and 646 of the electrodes, which helps to further lock the electrodes 604 in place and prevent the separation between the electrodes 604 and the electrode connection structures 616.

It is understood that the stimulation surfaces 626 of the electrodes 604 are exposed and not covered by the molding material 820. Again, as discussed above, the molding process according to the various aspects of the present disclosure results in very little to no molding flash on the stimulation surface 626 of the electrodes, which is an improvement over conventional electrode assembly fabrication processes.

Figure 49:
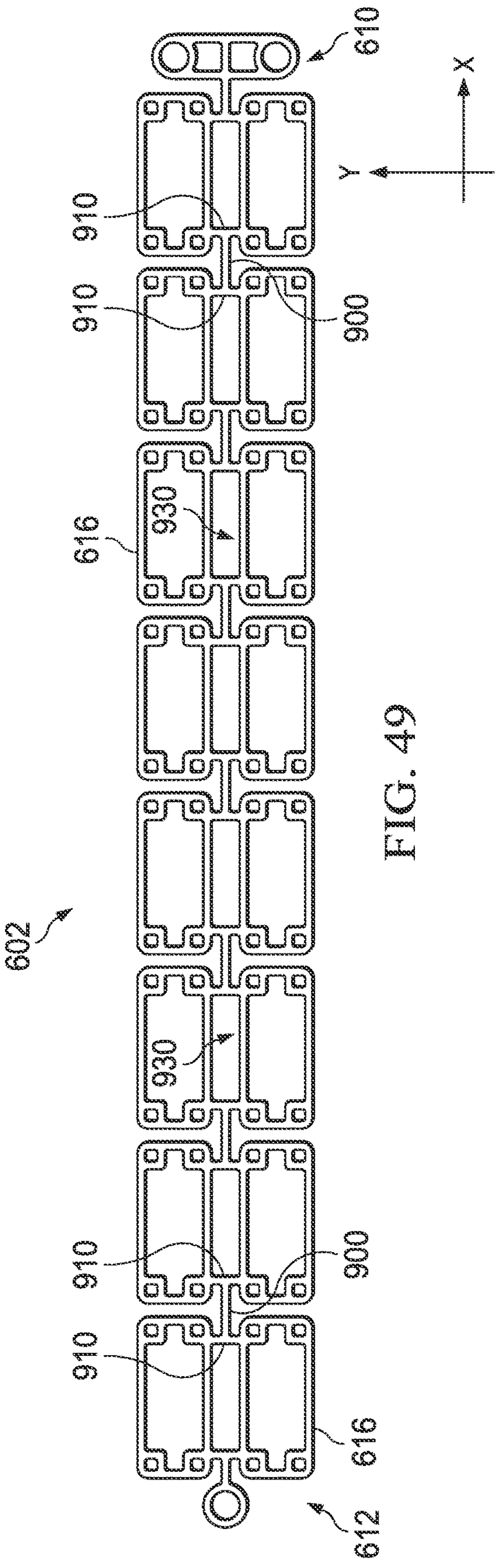
FIGS. 49-50 are planar top views of a substrate of an electrode assembly according to embodiments of the present disclosure.
Figure 50:
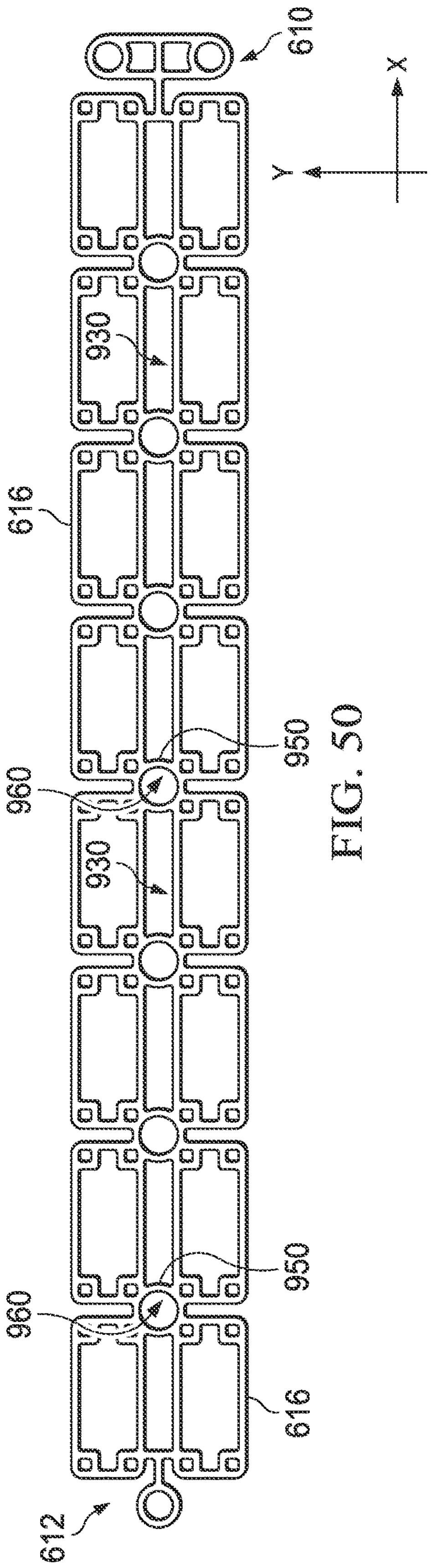

The discussions above pertain to an embodiment where the substrate 602 includes a single elongate stem portion 614. However, such an embodiment of the substrate 602 is not intended to be limiting, and other substrate configurations are also envisioned. For example, FIGS. 49-50 each illustrates an alternative embodiment of a substrate having a lattice structure/configuration. In more detail, FIGS. 49-50 illustrate planar top views (in an X-Y plane) of the alternative embodiments of the substrate 602. Rather than having a single elongate stem portion (such as the elongate stem portion 414 discussed above) that extends from the proximal end 610 to the distal end 612 in the X-direction, the substrates 602 of FIGS. 49-50 employ other mechanisms for coupling with the electrode connection structures 616.

For example, in the embodiment shown in FIG. 49, the substrate 602 includes a plurality of elongate stem portions 900 and a plurality of bridges 910. The elongate stem portions 900 each have a much shorter dimension in the X-direction than the single elongate stem portion 414 discussed above. Each electrode connection structure 616 is attached to respective ones of the elongate stem portions 900 through respective ones of the bridges 910. The elongate stem portions 900 and the bridges 910 collectively define a plurality of openings 930, which are located between respective pairs of electrode connection structures 616.

In the embodiment shown in FIG. 50, the substrate 602 includes a plurality of rounded structures 950 to mechanically couple the electrode connection structures 616 together. The rounded structures 950 define openings 960, which may be circularly shaped in the illustrated embodiment, but they may also be elliptically shaped or have other rounded shapes in different embodiments. The openings 930 disposed between adjacent pairs of the electrode connection structures 616 in the Y-direction also separate adjacent pairs of the rounded structures 950 in the X-direction. Again, the substrate 602 is devoid of a single elongate stem portion, but the rounded structures 950 are physically connected to the corners of the electrode connection structures 616, so that the substrate 602 is still a single piece of continuous structure.

Regardless of the specific embodiment used to implement the substrate 602, the inventive concepts of the present disclosure discussed above still apply. For example, the electrodes are still bonded to the substrate 602 (which may or may not have a lattice configuration such as shown in FIGS. 49-50) using a press fit or an interference fit, and the electrodes may still be implemented using the strip electrode concept discussed above, or as a different type of electrode.

Figure 51:
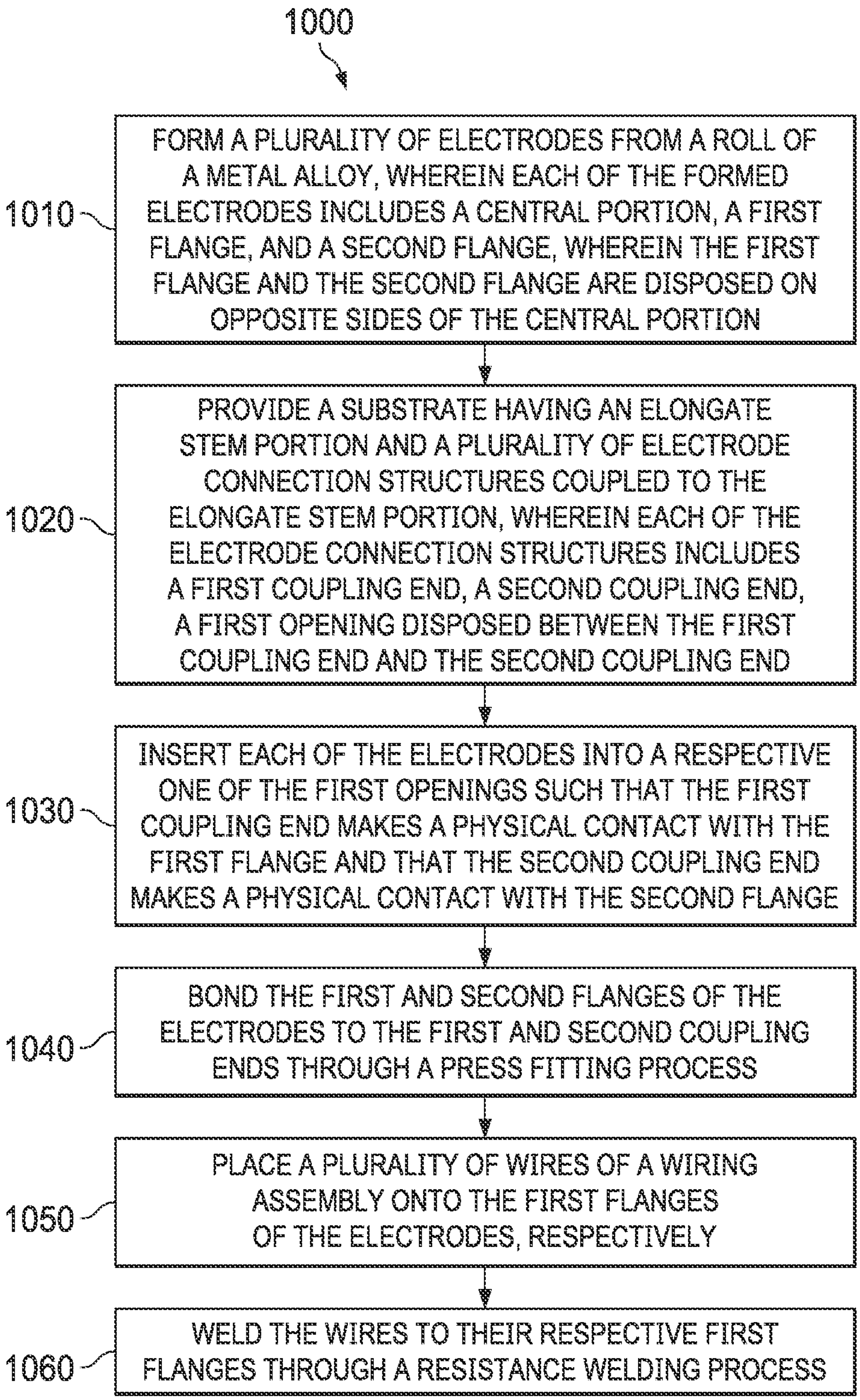
FIG. 51 is a flowchart illustrating a method of fabrication according to embodiments of the present disclosure.

FIG. 51 is a flowchart illustrating a method 1000 of fabricating an electrode assembly. The method 1000 includes a step 1010 to form a plurality of electrodes from a roll of a metal alloy. Each of the formed electrodes includes a central portion, a first flange, and a second flange. The first flange and the second flange are disposed on opposite sides of the central portion.

The method 1000 includes a step 1020 to provide a substrate having an elongate stem portion and a plurality of electrode connection structures coupled to the elongate stem portion. Each of the electrode connection structures includes a first coupling end, a second coupling end, a first opening disposed between the first coupling end and the second coupling end.

The method 1000 includes a step 1030 to insert each of the electrodes into a respective one of the first openings such that the first coupling end makes a physical contact with the first flange and that the second coupling end makes a physical contact with the second flange.

The method 1000 includes a step 1040 to bond the first and second flanges of the electrodes to the first and second coupling ends through a press fitting process.

The method 1000 includes a step 1050 to place a plurality of wires of a wiring assembly onto the first flanges of the electrodes, respectively.

The method 1000 includes a step to weld the wires to their respective first flanges through a resistance welding process.

In some embodiments, the electrodes are formed by: positioning the roll of metal alloy in a stamping machine, using the stamping machine to unwind the roll of metal alloy, using the stamping machine to form apertures within the metal alloy, thereafter cutting the roll of metal alloy into a plurality of electrode blanks with the apertures formed therein, and bending each of the electrode blanks to form the electrodes with the central portion and the first and second flanges.

In some embodiments, the substrate is provided by configuring the first coupling end and the second coupling end such that the first coupling end includes a second opening and a third opening, and the second coupling end includes a fourth opening and a fifth opening.

In some embodiments, the substrate is provided by configuring the first opening such that the first opening defines a first gap between the second opening and the third opening and defines a second gap between the fourth opening and the fifth opening.

In some embodiments, each of the electrodes further includes a first vertical wall portion joining the first flange with the central portion and a second vertical wall portion joining the second flange with the central portion. The first vertical wall includes a first aperture and the second vertical wall includes a second aperture. The first gap and the second gap are aligned with the first aperture and the second aperture, respectively.

It is understood that additional steps may be performed before, during, or after the steps 1010-1060. For example, in some embodiments, the method may include a step of performing an overmolding process to the electrode assembly, wherein the overmolding process is performed using a molding pin that is sized to press against a substantial entirety of an inside surface of one of the electrodes.

The electrode assemblies and the methods of fabrication thereof in the manner described in the present disclosure may offer advantages over conventional devices. However, it is understood that not all advantages are discussed herein, different embodiments may offer different advantages, and that no particular advantage is required for any embodiment. One advantage is that the formation of the strip electrodes herein reduces waste. Compared to conventional method of electrode fabrication that may result in a large amount of scrap material, the strip electrode formation process discussed herein generates very little waste. The roll-formed edges of the electrodes are also less likely to cause patient discomfort when implanted inside the patient.

Another advantage is enhanced structural performance. One of the unique design characteristics of some embodiments of the electrode assembly is that no portion of the substrate is disposed directly below the inside surface of the electrodes. The reduction in the surface area of the substrate allows the substrate to be made thicker to better tolerate the press/interference fitting processes to bond the electrodes to the substrate, while also preserving the flexibility and pliability of the overall electrode assembly. The elimination of the substrate under the electrodes also means that the molding material would not be pressed by the substrate against the electrodes. Accordingly, the electrodes are less likely to detach from the substrate. Furthermore, the electrode attachment structures themselves may be configured to have openings therein, which further increases the flexibility of the substrate and reduces the likelihood of the walls of the substrate being torn during various processes such as press fitting.

Yet another advantage is enhanced attachment between the electrodes and the substrate. For example, the electrodes are configured to have apertures on their vertical walls. The electrode attachment structures are also configured to have gaps that are aligned with the apertures, so that the molding material can flow into the apertures through the gaps. After the molding material is cured, the portions thereof that remain in the apertures of the electrodes provide another mechanism to attach the electrodes to the substrate, which again makes the detachment of the electrodes less likely to occur.

Several other advantages are attributed to the resistance welding of the electrode wiring. The resistance welding of the electrodes offers a strong bonding between the electrodes and their respective wires. In addition, this welding process may create a structurally weak point in each of the welded wires, and the excess portions of the wires may simply be snapped off, rather than having to use different lasers to cut the wires. Furthermore, since the wires may be welded onto the flanges of the electrodes, rather than on the inside surfaces of the horizontal portions of the electrodes that protrude over the substrate, there is now room on the inside surface of the electrodes to receive a much bigger molding pin. For example, the molding pin may come into physical contact with a substantial entirety of the inside surface of the electrode. This allows the molding components to have a much tighter fit, which then reduces the amount of undesirable molding flash on the stimulation surfaces of the electrodes.

Yet a further advantage is improved wire management. Compared to conventional electrode assemblies that have to glue the wires within various trenches or troughs, certain embodiments of the present disclosure simply use one or more banding mechanisms to tie the wiring bundle to an elongate stem portion of the substrate. The banding mechanisms may be in the form of a silicone girth hitch, or in the form of a silicone zip tie. The wiring management of the present disclosure allows the wires to be repositioned without much difficulty, which simplifies fabrication processes.

Other advantages may include compatibility with existing fabrication processes and the ease and low cost of implementation.

One aspect of the present disclosure pertains to a substrate configured to carry wiring and a plurality of electrodes. The substrate includes an elongate body extending from a first end to a second end in a first direction. The substrate also includes a plurality of electrode connection structures connected with the elongate body. Each electrode connection structure defines a first coupling end, a second coupling end, and a first opening positioned between the first coupling end and the second coupling end. The first opening is configured for insertion of a respective electrode. The first coupling end and the second coupling end are configured for physical attachment with the electrode inserted through the first opening.

Another aspect of the present disclosure pertains to an electrode assembly. The electrode assembly includes a substrate that includes an elongate body extending from a first end to a second end in a first direction and a plurality of electrode connection structures connected with the elongate body. Each electrode connection structure defines a first coupling end, a second coupling end, and a first opening positioned between the first coupling end and the second coupling end. The electrode assembly includes a plurality of electrodes positioned within the plurality of electrode connection structures, wherein a portion of each electrode extends through the first opening of the respective electrode connection structure. The electrode assembly further includes a wiring assembly extending along the substrate and forming an electrical connection with each of the plurality of the electrodes.

Yet another aspect of the present disclosure pertains to a method of fabricating an electrode assembly. The method includes forming a plurality of electrodes from a roll of a metal alloy. Each of the formed electrodes includes a central portion, a first flange, and a second flange. The first flange and the second flange are disposed on opposite sides of the central portion. The method includes providing a substrate having an elongate stem portion and a plurality of electrode connection structures coupled to the elongate stem portion. Each of the electrode connection structures includes a first coupling end, a second coupling end, a first opening disposed between the first coupling end and the second coupling end. The method includes inserting each of the electrodes into a respective one of the first openings such that the first coupling end makes a physical contact with the first flange and that the second coupling end makes a physical contact with the second flange. The method includes bonding the first and second flanges of the electrodes to the first and second coupling ends through a press fitting process. The method includes placing a plurality of wires of a wiring assembly onto the first flanges of the electrodes, respectively. The method includes welding the wires to their respective first flanges through a resistance welding process.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A method, comprising:

inserting an electrode through an opening of a substrate, wherein the electrode includes a central portion, a first flange, and a second flange, wherein the first flange and the second flange are disposed on opposite sides of the central portion;

bonding the first flange to a first coupling end of the substrate and bonding the second flange to a second coupling end of the substrate;

coupling a wire to the first flange; and performing an overmolding process, in which a molding pin is sized to press against a substantial majority of an inside surface of the electrode.

2. The method of claim 1, wherein the bonding is performed via a press fitting process or an interference fitting process.

3. The method of claim 1, wherein the coupling the wire is performed using a resistance welding process.

4. The method of claim 1, wherein the molding pin is sized to press against about 80% to about 100% of the inside surface of the electrode.

5. The method of claim 1, wherein the inside surface of the electrode faces in a direction toward the substrate.

6. The method of claim 1, further comprising forming the electrode at least in part by:

positioning a roll of metal alloy in a stamping machine;

unwinding the roll of metal alloy via the stamping machine;

forming an aperture within the metal alloy via the stamping machine;

cutting, after the aperture has been formed, the roll of metal alloy into a plurality of electrode blanks with the aperture formed therein; and bending each of the electrode blanks, thereby forming a plurality of electrodes that includes the electrode.

7. The method of claim 1, further comprising forming a second opening and a third opening in the first coupling end and forming a fourth opening and a fifth opening in the second coupling end.

8. The method of claim 7, wherein:

a first gap is disposed between the second opening and the third opening; and a second gap is disposed between the fourth opening and the fifth opening.

9. The method of claim 8, wherein:

the electrode further includes a first vertical wall portion joining the first flange with the central portion and a second vertical wall portion joining the second flange with the central portion;

the first vertical wall portion includes a first aperture and the second vertical wall portion includes a second aperture;

the first gap and the second gap are aligned with the first aperture and the second aperture, respectively;

a molding material is used in the overmolding process; and the molding material flows into the first aperture through the first gap or into the second aperture through the second gap.

10. The method of claim 1, further comprising: tying a wiring bundle that contains the wire to the substrate, wherein the tying is performed using a silicone girth hitch or using a silicone zip tie.

11. A method, comprising:

placing an electrode through an opening of a substrate, wherein the electrode includes a central portion, a first flange, and a second flange, wherein the first flange and the second flange are located on different sides of the central portion;

coupling the first flange to a first coupling end of the substrate;

coupling the second flange to a second coupling end of the substrate;

coupling a wire to the first flange; and pressing a molding pin against a substantial majority of an inside surface of the electrode.

12. The method of claim 11, wherein:

the first flange is coupled to the first coupling end of the substrate via a press fitting process or an interference fitting process; and the wire is coupled to the first flange via a resistance welding process.

13. The method of claim 11, wherein the substrate faces the inside surface of the electrode that the molding pin is pressed against.

14. The method of claim 11, further comprising, before the electrode is placed through the opening of the substrate:

positioning a roll of metal alloy in a stamping machine;

unwinding the roll of metal alloy via the stamping machine;

forming an aperture within the metal alloy via the stamping machine;

cutting, after the aperture has been formed, the roll of metal alloy into a plurality of electrode blanks with the aperture formed therein; and bending each of the electrode blanks, thereby forming a plurality of electrodes that includes the electrode.

15. The method of claim 11, further comprising forming a second opening and a third opening in the first coupling end and forming a fourth opening and a fifth opening in the second coupling end, wherein a first gap is formed between the second opening and the third opening, and wherein a second gap is formed between the fourth opening and the fifth opening.

16. The method of claim 15, wherein:

the electrode further includes a first vertical wall portion joining the first flange with the central portion and a second vertical wall portion joining the second flange with the central portion;

the first vertical wall portion includes a first aperture and the second vertical wall portion includes a second aperture;

the first gap and the second gap are aligned with the first aperture and the second aperture, respectively;

a molding material is used when the molding pin against the substantial majority of the inside surface of the electrode; and the molding material flows into the first aperture through the first gap or into the second aperture through the second gap.

17. The method of claim 11, tying a wiring bundle that contains the wire to the substrate, wherein the tying is performed using a silicone girth hitch or using a silicone zip tie.

18. A method, comprising:

inserting an electrode through an opening of a substrate, wherein the electrode includes a central segment, a first flange segment, and a second flange segment;

bonding, via a press fitting process or an interference fitting process, the first flange segment to a first portion of the substrate and bonding the second flange segment to a second portion of the substrate;

coupling, using a resistance welding process, a wire to the first flange segment; and performing an overmolding process, during which a molding pin is pressed against a majority of an inside surface of the electrode.

19. The method of claim 18, further comprising forming the electrode at least in part by:

positioning a roll of metal alloy in a stamping machine;

unwinding the roll of metal alloy via the stamping machine;

forming an aperture within the metal alloy via the stamping machine;

cutting, after the aperture has been formed, the roll of metal alloy into a plurality of electrode blanks with the aperture formed therein; and bending each of the electrode blanks, thereby forming a plurality of electrodes that includes the electrode.

20. The method of claim 18, further comprising forming a second opening and a third opening in the first portion of the substrate and forming a fourth opening and a fifth opening in the second portion of the substrate;

wherein:

a first gap is disposed between the second opening and the third opening;

a second gap is disposed between the fourth opening and the fifth opening;

the electrode further includes a first vertical wall portion joining the first flange segment with the central segment and a second vertical wall portion joining the second flange segment with the central segment;

the first vertical wall portion includes a first aperture and the second vertical wall portion includes a second aperture;

the first gap and the second gap are aligned with the first aperture and the second aperture, respectively;

a molding material is used in the overmolding process; and the molding material flows into the first aperture through the first gap or into the second aperture through the second gap.

* * * * *